US011887705B2

United States Patent
Davidovics et al.

(10) Patent No.: US 11,887,705 B2
(45) Date of Patent: *Jan. 30, 2024

(54) APPARATUS, SYSTEM AND METHOD FOR PATIENT-AUTHORIZED SECURE AND TIME-LIMITED ACCESS TO PATIENT MEDICAL RECORDS UTILIZING KEY ENCRYPTION

(71) Applicants: Bernard Davidovics, Boca Raton, FL (US); Ilya Aronovich, Great Neck, NY (US); William Frumkin, Great Neck, NY (US)

(72) Inventors: Bernard Davidovics, Boca Raton, FL (US); Ilya Aronovich, Great Neck, NY (US); William Frumkin, Great Neck, NY (US)

(73) Assignee: Ilya Aronovich, Great Neck, NY (US)

( * ) Notice: Subject to any disclaimer, the term of this patent is extended or adjusted under 35 U.S.C. 154(b) by 254 days.

This patent is subject to a terminal disclaimer.

(21) Appl. No.: 17/071,966

(22) Filed: Oct. 15, 2020

(65) Prior Publication Data

US 2021/0104304 A1 Apr. 8, 2021

Related U.S. Application Data

(63) Continuation-in-part of application No. 15/367,949, filed on Dec. 2, 2016, now Pat. No. 10,841,286.

(51) Int. Cl.
*G06F 21/00* (2013.01)
*H04L 9/32* (2006.01)
(Continued)

(52) U.S. Cl.
CPC ............ *G16H 10/60* (2018.01); *G16H 80/00* (2018.01); *H04L 9/0825* (2013.01);
(Continued)

(58) Field of Classification Search
CPC ........ G16H 10/60; G16H 80/00; G16H 40/20; G16H 40/67; H04L 9/0825; H04L 9/0894;
(Continued)

(56) References Cited

U.S. PATENT DOCUMENTS

| 2014/0257047 A1* | 9/2014 | Sillay | H04L 63/10 600/595 |
| 2015/0046192 A1* | 2/2015 | Raduchel | H04W 8/18 705/3 |
| 2022/0215948 A1* | 7/2022 | Bardot | G16H 40/67 |

FOREIGN PATENT DOCUMENTS

| WO | WO-2023085957 A1 * | 5/2023 | ............. G06F 21/00 |

OTHER PUBLICATIONS

Joseph A .Akinyele, Matthew W. Pagano, Matthew D. Green, Christoph U. Lehmann, Zachary N.J . Peterson, Aviel D. Rubin; Securing Electronic Medical Records Using Attribute-Based Encryption On Mobile Devices; ACM workshop on security and privacy in smartphones and mobile devices; Oct. 17, 2011; pp. 75-86 (Year: 2011).*

* cited by examiner

*Primary Examiner* — Fatoumata Traore
*Assistant Examiner* — Courtney D Fields

(57) ABSTRACT

A computerized system and method to allow patient to control and provide a safe, secure and efficient real-time access to the patient's private health records (PHR) stored in the encrypted uniform format in a Private Health Vault (PHV) database. The system utilizes patient's private encryption key for encrypting and decrypting PHR stored in the PHV. The patient (or patient's appointed agent) controls access to the PHR and authorizes by electronic communications with the PHV server to allow doctors to have access to the centrally maintained and structured medical data in the PHV. The access can be limited in duration.

(Continued)

The patient's private keys may be stored in a remote Key Bank database, separately form the PHV database, and the location of the patient's PHV data may also require transmission of the location id from a separate Mapping server. Additional security is provided by determining digital proximity of the doctor's and patient's mobile devices to the node device in the doctor's office, and terminating access upon set condition. It also utilizes 2-way digital token or id exchange and confirmation between the patent and doctor, as well as digital authentication for access and identity verification. The centralized PHV stores patient data more efficiently and prevents unauthorized use of the patient data by separating the key(s) needed to decrypt patient data from the actual patient records in the PHV.

18 Claims, 16 Drawing Sheets

(51) Int. Cl.
    *G16H 10/60*    (2018.01)
    *H04L 9/08*    (2006.01)
    *H04W 4/80*    (2018.01)
    *G16H 80/00*    (2018.01)
    *G06F 21/62*    (2013.01)

(52) U.S. Cl.
    CPC .............. *H04L 9/0894* (2013.01); *H04W 4/80* (2018.02); *H04L 2209/80* (2013.01)

(58) Field of Classification Search
    CPC ........... H04L 2209/80; H04L 2209/805; H04L 63/0442; H04L 63/068; H04L 63/10; H04L 2209/88; H04L 9/0891; H04L 67/10; H04L 67/12; H04W 4/80; H04W 12/06; H04W 12/08; H04W 12/63
    See application file for complete search history.

APPARATUS, SYSTEM AND METHOD FOR PATIENT-AUTHORIZED SECURE AND TIME-LIMITED ACCESS TO PATIENT MEDICAL RECORDS UTILIZING KEY ENCRYPTION

PRIORITY

This application claims priority under 35 U.S.C. § 120 of U.S. patent application Ser. No. 15/367,949, filed on Dec. 2, 2016, entitled "A Method, Device and System for Secure Universal Exchange of Patient's Medical Records Utilizing Encryption Technology", which claims priority under 35 U.S.C. § 119(e) of the provisional patent application No. 62/262,021 filed on Dec. 2, 2015, entitled "A Method, Device and System to Provide Patients with Secure Access to Their Digital Medical Records," provisional patent application No. 62/287,904, filed on Jan. 28, 2016, entitled "A System and Method for Secure Exchange of Patient Medical Records" and provisional patent application No. 62/326,002, filed on Apr. 22, 2016, entitled "A System and Method for Secure Exchange of Patient Medical Records."

FIELD OF THE INVENTION

The present invention pertains generally to an apparatuses, methods, and systems for maintaining a secure and efficient distributed Internet cloud database containing patient's medical records, and providing encrypted key authorization to have a secure and efficient access to all patient's records. More specifically, the invention relates to a system and method that utilizes novel use of private key encryption and novel use of public and private keys for secure transmissions, which enable the patients to fully control access to their own medical records in a secure Internet cloud storage, and also to grant doctors, hospitals, pharmacies and other medical and health care service providers quick and efficient "on purpose" or "on demand" limited and temporary access to the patients' medical records when needed. This allows the patients to maintain and control access to the centralized and secure database holding the latest patient's medical records, which updated and accessed in real time by the health care service providers with automated real-time authorization given by each patient.

BACKGROUND OF THE INVENTION

In the modern world, there are numerous, often duplicative and incomplete, repositories of medical information about a particular patent. These records are kept by different hospitals where the patient is admitted or undergoes treatments, doctors who provide out-patient services or conduct medical tests and procedures, pharmacies that fill out prescriptions, and other medical and alternative medicinal service providers where the patient undergoes treatments. This system gets even more complicated when a particular patient changes residence, moves to a different state or travels to another country and undergoes medical treatments in different geographic locations by different doctors.

One of many challenges that a modern medical system tries to solve is maintaining a central and complete database or some other records of all medical treatments, tests, diagnostics, procedures, medications and alternative medicinal treatments for a particular patent. Unfortunately, due to privacy restrictions, federal and state regulations, hospital and other medical providers' internal policies and simply due to patient's inability to remember all healthcare providers that he or she used in the past makes this nearly impossible.

On one hand, patient's health records (PHR) must be secure and private, and, on the other, it is critical that any doctor, who needs to treat a patient, have complete and accurate information of the patient's medical history, conditions, treatments, allergies and medications. Furthermore, PHR must be current, accurate and complete, and available in real time to every Health Care Provider, doctor, medical staff, hospital, pharmacy, patient advocate and others. At the same time, the access to these records must be strictly protected against unauthorized user and access by anyone who is not immediately authorized to access PHR by the patient. Until now, by replicating data in multiple places, and allowing different medical institutions and their IT service providers to have access to PHR, the risk of misuse and unauthorized access to PHR becomes often very high. While many technology companies (Microsoft, Google), Medical Record companies (Epic, McKesson etc.), Health Information Exchanges (243 in 50 states), and Patient Health Record companies (CareZone, CareSync, FlowHealth) have spent millions of dollars on setting up central repositories of PHR or coordinating and exchanging PHR data between numerous different medical providers, the coordination and security efforts have not yielded an efficient and secure system for the exchange of and access to PHR for On Purpose Secure Access (OPSA). The OPSA mandates proving secure access to medical records to doctors, pharmacies, hospitals and other medical and Health Care Providers (HCPs) for a specific purpose at a specific time, at a specific place. Thus, there is a very strong need and demand for such a secure system, which maintains PHR for a patient and allows OPSA access when a patient visits a doctor for treatment, goes to the hospital, pharmacy or needs to discuss medical matters with a patient health care advisor or advocate.

A number of current companies offer a centralized Internet repository for medical data, where HCPs can store medical data. These companies try to collect and aggregate data from multiple HCPs, to allow one centralized access point. However, this approach does not meet the security requirements and often exposes HCPs to liability because they need to open up their portals and expose their patients' medical records to the Internet, which is prone to abuse and misuse by hackers, who try to gain unauthorized access to medical records. Similarly, when HCPs provide copies of their PHR to a Health Information Exchange, the patients' data becomes ultimately accessible to Internet users, which poses the same problems as discussed above.

Some currently known systems, such as Care Zone, allow a patient to "invite" a doctor to share their patient's medical data. However, these systems require granting to the doctor and his agents the authorization using their userid and password. Therefore, as the patient invites more and more doctors to have access and share patient's medical records, there are more and more userid's/passwords issued by the patient to access their PHR. This geometrically increases the possibility of a hacker to access patient's PHR by illegally obtaining one of the userids/passwords provided by the patient to one of many doctors or healthcare providers, or when those providers hire or use IT or support service personnel to access and update the patient's PHR using the userid/password given to the doctor or health provider organization. Thus, the risk of a breach of data increases geometrically with each additional invite. This technological problem is particularly acute in medical and health care regulated industry, where HCPs are regulated and required to maintain and protect patient health care information, and where mistakes or errors, or lack of complete information and access to patient data can have dire consequences to patient's health and treatment.

The federal mandated patient portal creates a similar problem from another side. As currently implemented, the patient must access multiple portals for multiple doctors. Patients typically can't remember all the passwords—so they either write them down or choose passwords (or just one password) that are "easily" remembered, such as based on date of birth, names of family members, etc., which are "easily hackable" variations that can be broken and illegally accessed by unauthorized persons.

In many current systems the medical records and medication records are associated with all patients' personal information. Which means that a hacker that gains access to the database—gains access to personal and medical information of tens or hundreds of thousands of patients. This high concern for the global nature and impact of possible invasive action by hackers led to the systems such as those described in the U.S. Pat. No. 6,874,085 ("Medical Records Data security system"), which suggest separating the PHR into two parts: the "personal data" part and the "medical data"—portions. In that case, they provide security by putting extra layers of security on the "personal portion"—to make it harder to decipher what medical record belongs to which patient. However, the personal data is still kept in the same database and like all things, it can be copies and hacked—and the doctor or HCP—may share the risk and liability for such a breach.

Thus, there is a strong need for a system that would enable a patient to authorize and provide OPSA access to only his own records, and not to the aggregate dataset containing records of thousands or millions of other patients. This secure and efficient approach also reduces the potential for misuse or abuse because it does not allow someone posing as a patient or medical professional, or some unscrupulous medical professional or IT support person for a HCP gain access without a specific patent's authorization, and under no circumstances allows access to any other patient's records.

There is also a need for a centralized and efficient PHR data management system that is capable of storing information and PHR data of multiple patients, but would allow access only to one PHR based on patient's authenticated real-time authorization. There is also a need for a single system that automatically organizes and unites patient's records stored in disparate sources and possibly incompatible databases or data models of different providers that store patient's medical records (or part of medical records of the same patient).

Furthermore, in most current systems, the doctor, Health Care Provider (HCP) or billing company owns and controls the data, access to data, and is responsible to keep it secure. On the legal side, the HCP is responsible for the data and is liable to the patient if it is breached. Each HCP spends tremendous amount of funds and resources on keeping the PHRs that it keeps for its patients secure, and this effort is duplicated across multiple HCPs. This results in extraordinary waste of financial resources and duplication of technical efforts and work. The consolidation or introduction of another security system for any HCP typically creates only additional expenses. HCP is required by law to keep its all prior data secure and also must keep secure the new data repository until the data is moved from one system or database to another. The costs for such transitions are very high and taxing on IT personnel retained by HCPs. Thus, there is a need for a simpler system that does not impose such high burden on HCPs and also allows for a seamless transition to a new system, without wholesale movement of patient data to a new system.

Also, in the current systems, the patient may authorize the doctor in person or on a phone, without any traceable audit trail and proof of actual authorization being conveyed. Furthermore, the patient may provide the email address to the doctor and make an error and send authorization to someone else. Even when the authorization (userid and password for access to PHR) is sent to the correct email, there are general risks inherent in all Internet transmissions, including transmitting it across a multitude of network connections and storing in a multitude of servers before it arrives at the intended destination. Also, when the email arrives to the doctor's office, it may be accessed by others, and may be subject to break in by hackers or someone else with malicious and illegal intentions. Thus, there is a need for a system that is more secure and avoids some of these inherent risks of the current systems.

There is also a need for an automated computerized system that would allow different patients to store their PHR data in secure and encrypted format in a separate database, and making it easy for each patient to allow different HCPs to access this data and update it with new medical information, such as new treatments, prescriptions, medical test results, etc. It is further needed to allow patients to save and store their private "access key" or any decryption electronic access id or key for access to their PHR data in a secure manner, utilizing a computerized system that prevents and minimizes possible breaches and unauthorized access to PHR data for multiple patients.

There is also a need for an automated computerized system that would allow different patients to store their PHR data in secure and encrypted format in a central location, and use only one key, userid or security code, instead of remembering and keeping multiple ones for each doctor and HCP who treats the patient. It is further desirable to provide an automated secure location that allows patients to store their key, userid or security code for access to their PHR data that is separately stored in a Private Health Vault (PHV) in encrypted format, and where the patient's stored PHR can't be accessed or read without proper private key, userid or security codes of the patient. Additionally, there is a need to provide extra security measures that would further protect the PHR data of each patient stored in PHV even when someone illegally obtains the private key, userid or security code of the patient.

There is also a need for an automated computerized system that would allows a unified and structured access and storage of medical records from the multiple databases of HCPs, and automatic updates of medical data. There is also a need for an automated computerized system that remove private information or patient identification information for the purposes of using patient's medical records for the research and other public and scientific purposes.

SUMMARY OF THE INVENTION

It is an object of the present invention to provide an Internet cloud-based system that will allow a safe, secure and efficient immediate real-time access for a patient to obtain, keep and share his up-to-date PHR, including prescribed medication information with different doctors, pharmacies and other health services providers. The PHR data may be kept in a specialized computerized system of the present invention, in a remote digital Health Vault database, referenced herein as the Private Health Vault (PHV), where each patient's PHR records are encrypted using private digital key or some other private encryption process that is known and controlled by the patient, wherein the access for doctors and HCPs to the PHR records in the PHV are controlled by the patient.

It is an object of the present invention to provide a single system that organizes and unites patient's records, using software and/or Artificial Intelligence, where the medical records are stored in disparate sources and possibly incompatible databases or data models of different providers that store patient's medical records (or part of medical records of the same patient).

It is also an object of the present invention to provide a system that allows the patient to set up a Web-based application on a mobile device, such as for example a smartphone or tablet, or real-time access via Internet browser the database with PHR, and also to be able to share this data with another doctor or other HCP, and particularly checking and updating the list of prescribed medications, treatments or test results for the particular patient. It is further desired that this system allows for a quick and efficient access to patient's PHR, so that the patient can quickly set up, update and upload medical data that is maintained by a particular doctor or hospital to the other PHR for the patient, thereby keeping the complete and up-to-date PHR for the patent. This also allows doctors that treat the same patient to obtain the latest updated patient's PHR records, without any need to request latest updates from another HCP who may have recently treated the same patient.

It is another object of the present invention to provide a real-time system and method wherein the patent, rather than multiple HCPs and their IT departments, owns and controls the PHR, access and authorizations to that patient's PHR. Furthermore, the patient has the ability to limit access to only a subset of PHR information for any of that patients medical services provider, and can share view and or update capabilities with the doctor for a "purpose" limited to a particular time and place, like, for example, during a doctor's visit, hospital treatment or a visit to pharmacy.

It is further object of the present invention to allow a specialized computerized system that allows a patient to use his or her mobile device, such as iPhone, Android, tablet or other mobile or desktop computer processor device to permit a particular doctor or HCP to access patient's PHR, authorize it through a simple screen authorization procedure on the patient's mobile or desktop computerized device, but limit the access to the time that the patient visits PHR or for a short fixed time after or during the visit to HCP. The doctor and patient only need to download the specific SMR app or software once for their device. Then, the system will automatically track the patient's presence in the HCP's facility and allow patient to view the doctor's information on the patient's mobile or desktop computer device and authorize doctor or HCP to access patient's PHR during the visit by entering the doctor's id or clicking on the authorization screen for the specific doctor or HCP facility registered with SMR service.

The present system and method also does not affect doctors' or hospitals' patient information that is required to be kept by law or regulation, and is already in the doctor's EMR. Each doctor and each EMR may have only a subset of the PHR for a particular patient, while the patient may control and have access to the more complete PHR and can share it with others HCPs for a "purpose." Unlike the current systems like Care Zone, the present invention does not give doctors the access with their own userid and password for access to PHR. As discussed in the Background of the invention, the sharing and granting access to multiple HCPs, doctors, and other health services providers with their own userids and passwords creates a higher chance for misuse and unauthorized access by individuals who may steal the userid/password and gain unauthorized access. The present invention only allows the patient to grant the access for a "purpose" during the limited time when the patient is physically present in the doctor's office, and removing all access authorizations after the patient leaves the doctor's office, but keeping PHR accessible by the patient and capable of sharing with other doctors or HCPs in the future. Thus, patient's PHR is kept in a secure preferably cloud-based database or PHV (as referenced in this specification), and allow different HCPs only the "on purpose" secure access, which is limited in duration by the patient. The limited duration of such "on purpose" secure access is particularly important when patients allow pharmacy to access their PHR during a pharmacy visit, but do not want the pharmacy to have full access to this data at all times, and particularly after the prescription is filled and received by the patient.

It is also an additional object of the present invention is to allow HCPs who keep their own EMR patient data to set up quick upload into the SMR PHV, but utilizing private key of each patient for encryption of each patient's PHR data in order to make such upload secure and tamper-resistant. Another object is to allow HCP to move the patient data from EMR to a more secure SMR PHV, which can only be decrypted using a private symmetric key held by the HCP. It may also provide copying individual patient records in doctor's PHV to patient's PHV, where the PHR of the patient are re-encrypted with patient's symmetric private key, and stored in SMR PHV, where the access to patient's copy of his PHR data is owned by the patient and the access can be given by the patient to multiple HCPs.

Yet another object of the present invention is a system that allows a patient to controls access to their PHR data stored in the cloud on the Internet. Essentially, it enables the patient to carry around a "virtual folder," i.e. access to the PHR of the patient, which the patient allow to access and share with a doctor while the patient is physically present at the doctor's office. It also allows the doctor to view and update patient's PHR in this so-called virtual medical folder of PHR. Once the update is done, the doctor or anyone at the doctor's medical facilities will no longer have access to the patient's PHR. Furthermore, this process and method would not require changing or setting up new passwords or access privileges, which is problematic with current systems. The computerized system of the present invention also reduces the exponentially growing risk of a breach due to granting full and perpetual access rights to PHR for each new doctor and HCP.

To achieve some of these objectives, the present invention puts the Patient is in control and responsible for the security of their PHR information. The SMR Access system according to present invention provides an easy and secure mechanism for the patient to provide access to the doctors and other medical providers to view, add and update the patient's PHR data. Instead of the doctor providing access for the patient, the patient is choosing if when and how to trust the doctor with access to the patient's PHR data. Instead of the doctor controlling access and being liable for any breaches or unauthorized use—the patient control's access and is responsible for the security of their data, thereby reducing doctor's risk and exposure to legal liability for breaches or loss of patient's PHR data.

The doctor/HCP will continues to be responsible and liable for the patient data they keep in their EMR. However, by utilizing SMR Access system according to the present invention for future access to patient's records and reducing Internet based transmissions of authorization information and PHR, the risks and exposure for the doctor/HCP is reduced. In the SMR system, the patient chooses if, when and what data that he authorizes the doctor/HCP to transfer to the patients control. The SMR system provides a safe, simple and secure mechanism for the patient to control access to his or her PHR records and data, and to securely authenticate and know who is authorized to access and update the PHR data.

The SMR system also provides an audit trail to the doctor/HCP to prove that the doctor/HCP has acted with the proper authorization from the patient. For example, in the present systems, a patient may ask a doctor to email them a copy of their blood test. The use of email in such cases is "acceptable"—because of a direct person-to-person or voice-to-voice authentication between the patient and the doctor or doctor's staff. Essentially, the patient is authorizing the doctor to put the blood test results into the public domain on the public Internet. It is the patient authorizing the doctor to transmit the blood test results through the Internet. Of course, the patient is assuming all the risks associated with unsecure Internet email transmissions. However, most people are not aware of all security problems associated with Internet emails. They simply do not consider what happens when the doctor or staff sends the email accidentally to the wrong email address, and typically presume that the doctor would be liable for the exposure due to such actions. The doctor, on the other hand, would face difficulties in proving that in fact the patient took the responsibility and the risk of emailing the test results via Internet email. The current invention, improves upon the current mechanism that patients use today to authorize a doctor to provide them their medical records.

The SMR system according to present invention utilizes and combines in a novel way some of the features of known technologies to implement a system that provides a significantly higher degree of assurance that:

The patient knows that he is authorizing the correct doctor/staff
The doctor knows that it is the actual patient authorizing the transfer
That the entire transfer of data is audited and logged
That the patient understands and accepts the risk of the transfer
That the doctor is not liable for breaches caused by the patients carelessness The present SMR also provides the greater levels of security without imposing additional undue burdens of complexity on the patient or doctor/HCP.

The present SMR system and invention could use any of the following modes of authentication:
What you know (password)
What you have (Smart/Cell phone, keyfob, etc.)
What you are (Fingerprint)
What you can electronically perceive (as for example, proximity detection of devices in actual geographic vicinity).

This means that in addition to having your cell phone, your smart phone can perceive the electromagnetic pulses emanating from the doctor's WiFi access point or Bluetooth Beacon or other electronic signature. The process by which the patient is authenticated and is able to authenticate and authorize the HCP to view and update the patient's PHR depends in part on the WiFi and bluetooth signatures being seen by the patients, their smart phones and HCP devices, which would allow to establish and verify electronically the physical vicinity of the devices and persons operating those devices (ex. patient, doctor, doctor's office, pharmacy, etc.)

The present SMR system further provides secure real-time access by time. Unlike current methods where a patient might invite a doctor to view/update records by providing them doctor with username and password, the current invention provides for the patient to provide the doctor or HCP access only for a defined period of time—and while the patient is at the doctor's office. This allows "On Purpose Secure Access," and assures that the access to PHR is used only by the doctor for its intended purpose. If the doctor or patient discards the temporary password, then it cannot be used.

The present SMR system may utilize several well known and public cryptographic security technologies to accomplish the above, and also to use the following:
Public and Private Key Infrastructure (PKI)
Secure Socket Layer (SSL)
Cryptographic Hash Technology
Bitcoin Protocol
WiFi, Bluetooth and other Indoor location technologies
Mobile Technologies In all the known and currently used systems, the doctor, HCP or billing company owns and controls the PHR data of the patient, and also carries the legally required confidentiality and security obligations to protect access to this data. If breached, the doctor, HCP or billing company may have legal responsibility for the breach. In contrast, the computerized software solution of the present invention allows the doctor or some other HCP (including, without limitation, the pharmacies) to access PHR only temporarily, based on patient's authorization. Thus, it allows the patient to control access to his or her PHR, while reducing risks of unauthorized breach, exposure risks for multiple patients, and providing the patient with the ownership and easy administration of access priorities to the patient's PHR. Furthermore, the present invention protects the access to PHR not simply based on some username and password combination, but also based on the patient device's proximity to the doctor's or PHC's authorized WiFi network and the express authorization by the patient while in such proximity. In fact, the present invention uses multiple modes of authentication:

(1) What you know (password, secure id or key)
(2) What your have (patient's or doctor's mobile device, keyfob, patient's computer, etc.)
(3) What you are (patient's or doctor's fingerprint or direct authorization while at the PHC facility)
(4) What you can electronically perceive (patient's mobile device or computer received certain WiFi, Bluetooth or other signals or some other electromagnetic, electronic, UV, IR or some other electronic signature signal directly from the computer at the PHC location); electronic proximity detector identifying the device in the geographic proximity Another aspect of the present invention is the provision of audit trail for the doctor or HCP, to confirm that they acted with the authority of the patient. This significantly reduces the doctor's or HCP's exposure for any breach. Furthermore, because each patient provides his or her personal authorization, and HCP or doctor are not required to maintain a full database of all patients' PHR, the overall risk of a breach and theft of all patients' PHR is significantly reduced and/or eliminated for the doctor or HCP.

The Key Vault aspect or feature of the present invention also allows multiple patients to safeguard and store their "access keys" (or password or some electronic information that allows access to PHC data) in a secure and private manner, without the need to maintain multiple passwords or access keys for different subsets of patient's PHR maintained by different doctors, hospitals, pharmacies, billing companies, etc.

Another feature of the present system is to allow patients to save their "access keys" (or electronic id, token or other types of digital access key data) in a particular database or memory location, and also maintain a separate mapping server and database, which allows the authenticated owner of the PHR (like a particular patient), to obtain the identification or location id of the PHR data records of that patient that are stored in the PHV. This way, the system protects patients PHR data in the PHV even if someone illegally obtains the private key of a particular patient. Thus, in order to actually gain access to the patient's PHR data, the system requires both the private key of the PHR data owner and the authorized mapping or location ids of the stored patient's records in the PHV.

Another feature of the present invention is use of a digital fingerprint data (or some other electronic identification information, such as image, retina scan, etc.) for the person operating the mobile device of the patient and doctor, to make sure that it is actually the authorizing person or authorized HCPs requesting or authorizing access to the PHR data from the PHV server, using authenticated patient's or doctor's mobile device or computer. The fingerprint authorization technology (or other electronic identification technology) also allows patients and HCPs to switch mobile devices or computers, without the need to redo the full authorization process with each new device, and to use someone else's mobile device or computer for authorization and access to PHV. The authenticating digital fingerprint (or other personal identification methods, like facial recognition, retina scan, etc.) may be security sent to the authentication server, where it is compared to the patient's and/or doctor's fingerprint or other electronic identification data provided during registration, thereby assuring that the person operating the device and requesting access to PHR is the correct person.

Another feature of the present invention is to provide an automated computerized system that utilizes an automated software or AI to separate structured and unstructured data in multiple databases of HCPs into a structured data stored in the PHV, and utilizes the automated software and AI for structuring, migration process and for communication with individual HCP's systems through a user interface, as well as for automatic updates of the individual HCPs with any changes or additions to the patient's records.

Yet another feature of the present invention is to provide an automated computerized system that allows the automated software or AI to process patient records and remove private information or patient identification information, wherein the data can be shared with others for research and other purposes. It also allows the patient to establish a trustee for the access to patient's medical records and for granting access rights to HCPs and time-based and limited access to the patient's PHV and medical records.

These and other beneficial features and advantages of the present invention are disclosed in detail hereinafter with reference to the accompanying drawings and descriptive matter in each embodiment of the invention.

DETAILED DESCRIPTION OF THE INVENTION

A. Data Storage Architecture

Figure 1:
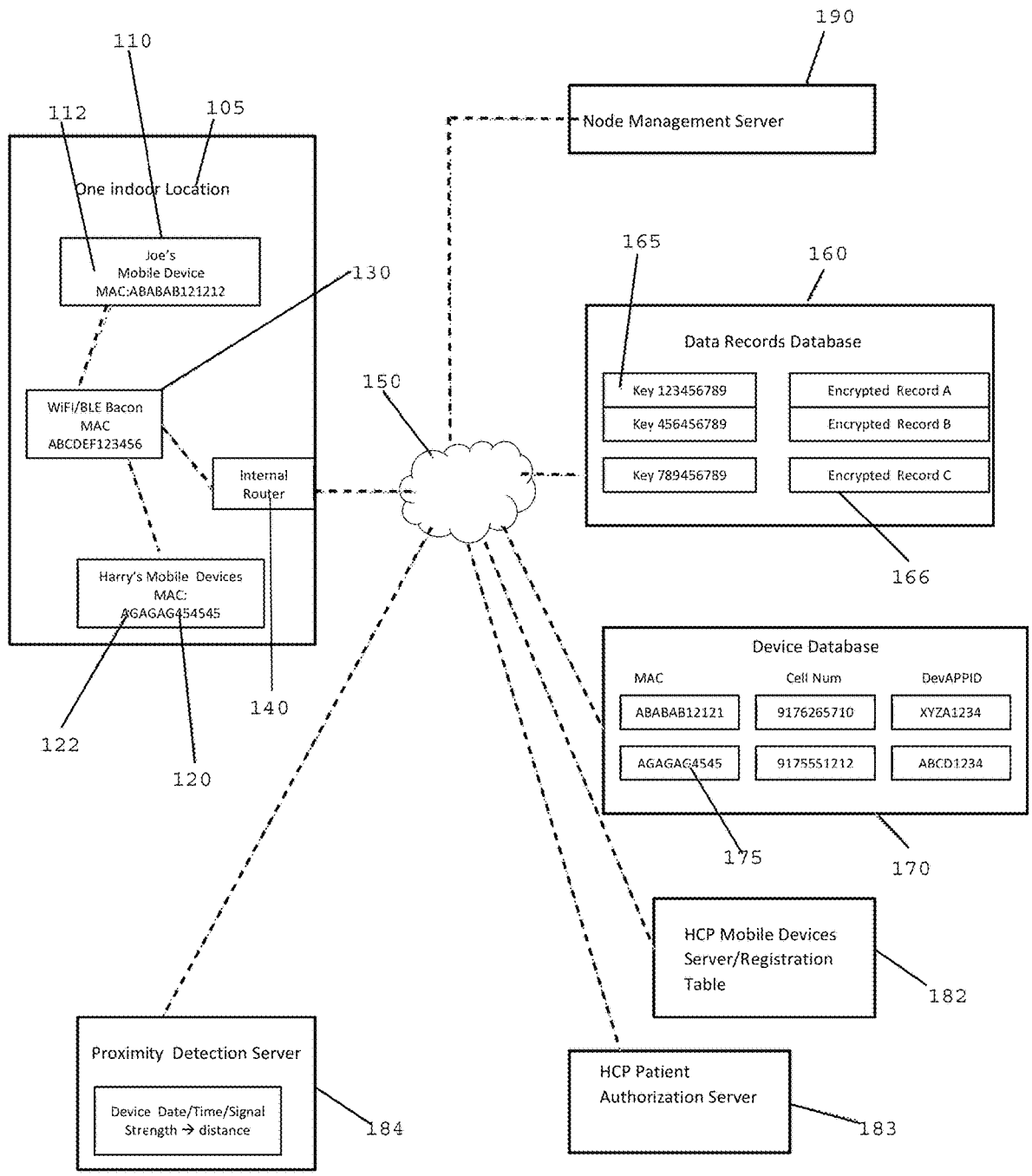
FIG. 1 illustrates a diagram of a cloud architecture and overall data storage architecture for storing SMR patient medical records in accordance with at least one embodiment of the present invention.

A general Internet cloud architecture and data storage organization for storing patients' PHRs in a "Patient Health Vault" (PHV) in accordance with at least one embodiment of the present invention is described with reference to FIG. 1. A number of different patients may be present in the doctor's or HCP's office 105. FIG. 1 shows two patients with mobile devices 110 and 120, such as smartphones, tablets, portable computers or similar Internet enabled devices. Each portable device 110 and 120 has its unique MAC address, shown as 112 and 122 for the devices 110 and 120. The server and/or a computer device in the doctor's office 130 (node) has its own MAC address and may communicate via WiFi with the mobile devices 110 and 120, and through the Internet router 140 at the doctor's or HCP's office and the Internet 150, to the Proximity Detection Server 184, HCP Authorization Server 183, HCP Mobile Devices Server 182, HCR Data Records Database 160 and Device Information Database 170. The communication through the Internet at the doctor's or HCP's office may also proceed through any Internet-enabled device, server, network, router, LAN, or any number of wired or wireless configurations that allow mobile devices of patients to access and communicate through the Internet. While the WiFi RF communication is preferred, other means of communications via RF, such as Bluetooth, IR or ultrasound may also be used, with different types of communication protocols. For example, without limiting to any specific, protocol, the patient mobile devices may also communicate with the computer in the doctor or HCP office via Bluetooth protocol, via ultrasound, or could also link by wired connection (for example, through USB or Ethernet connection) to the computer (node) 130 in the doctor or HCP office.

In one preferred embodiment, the computer device (node) 130 in the doctor's or HCP office receives signals and communications from the patient mobile devices 110 and 120 and may access the Proximity Detection Server 184 at which the signal strength of the received device signals is evaluated, in one embodiment based on the signal strength, and then generating a list of the user or patient devices that are detected or known to it that are present in the proximity to the HCP computer device (node) 130. The communication with the Proximity Detection Server 184 may proceed via router 140 and Internet 150 or could be based on the direct local area network connection (or a distributed computer network) in the HCP office. The Proximity Detection Server could perform the proximity evaluation based on the date, time and signal strength data received from the computer device (node) 130 for each patient mobile device 110 and 120, and all others in the proximity and communicating with it. In one embodiment, the signal strength is evaluated to determine the distance between the computer device (node) 130 and each patient mobile device 110 and 120. The present system may also utilize other types of distance evaluation techniques that are known in the industry, such as for example positional triangulation based on time delay of the received electromagnetic signals, such as RF, IR, US (ultrasound) and other types of electronic communication signals and data transfer methods.

In one preferred embodiment, the patient PHR data is stored and protected in the cloud-based PHV and can be downloaded from it to the patient's mobile or stationary device. Each patient record in the data store (PHV) is encrypted with an asymmetric key that is unique for each patient. The digital version of the patients' records is encrypted using the PKI asymmetric architecture. The encryption assures that even if the entire PHV database were to be hacked by an unauthorized person, or even all the hard disks containing the database were to be hacked or downloaded or stolen—still the data would be useless without having each patient's individual private key to decode the PHR data.

As shown in FIG. 1, in accordance with one of the embodiments of the present invention, the information about patients is preferably separated into different databases, the Private Health Vault (PHV) or Data Records Database 160, showing encrypted Records different patients' records A, B and C 166, each encrypted with the patient's symmetric crypto key, and also contains record locator id (or location key) 165. The patients' records are identified by a "record locator number or id" and not any personally identifiable information. Each different patient's record is encrypted separately with it's own owner's symmetric encryption key and also identified by the record location id (or location key) 165. Thus, the patient owns and controls access to his encrypted PHR data stored in the Data Record Database 160 by controlling the symmetric private crypto key and also through the required authorization and mapping process, where the patient is authenticated and then the mapping is provided to the actual Encrypted Records A, B, or C 166 for the patient. In the preferred embodiment, the data architecture utilized by SMR does not include any personal information such as patient name, address etc. The data is only identified and can be accessed by anonymous key—known only and kept only by the patient. As an additional level of protection, there may be mapping information, which maps the authenticated owner (patient) to the record location ids (or keys) 165 that identify the specific PHR records for that patient. However, even if actual records of the patient are identified and mapped, to actually decrypt and either read of update the patient's records, the anonymous electronic key or id, such as for example the symmetric digital key of the patient is still required.

The Device Database 170 is preferably a separate database or file system on a server that contains specific identification information for each device and telephone number of the patient whose information and PHR is kept in the Data Records Database 160. It may also contain device information about the doctor's or HCP's mobile device or computer that is registered with SMR services, and may utilize the present system for PHV records storage. In one embodiment, the specific identification information stored in the Device Database for each device is a MAC address corresponding to the patient's or doctor's smart phone or computer device. In one embodiment, the Device Database 170 also contains information about node 130 and all mobile devices of either patients or doctors that are in the electronic proximity of the node 130, and consequently in the geographic proximity to each other.

In one embodiment of the present invention, the Data Records Database 170 may be a distributed database stored on the Internet cloud, to provide an extra level of security against unauthorized copying of multiple patients' data. However, a conventional database, databases, or file storage system may also be utilizes. The Device Database may contain information about the doctor or HCP, such as physical location, office, name of the treating physician, pharmacy identification, pharmacist identification information and other data that identifies the HCP.

Figure 9:
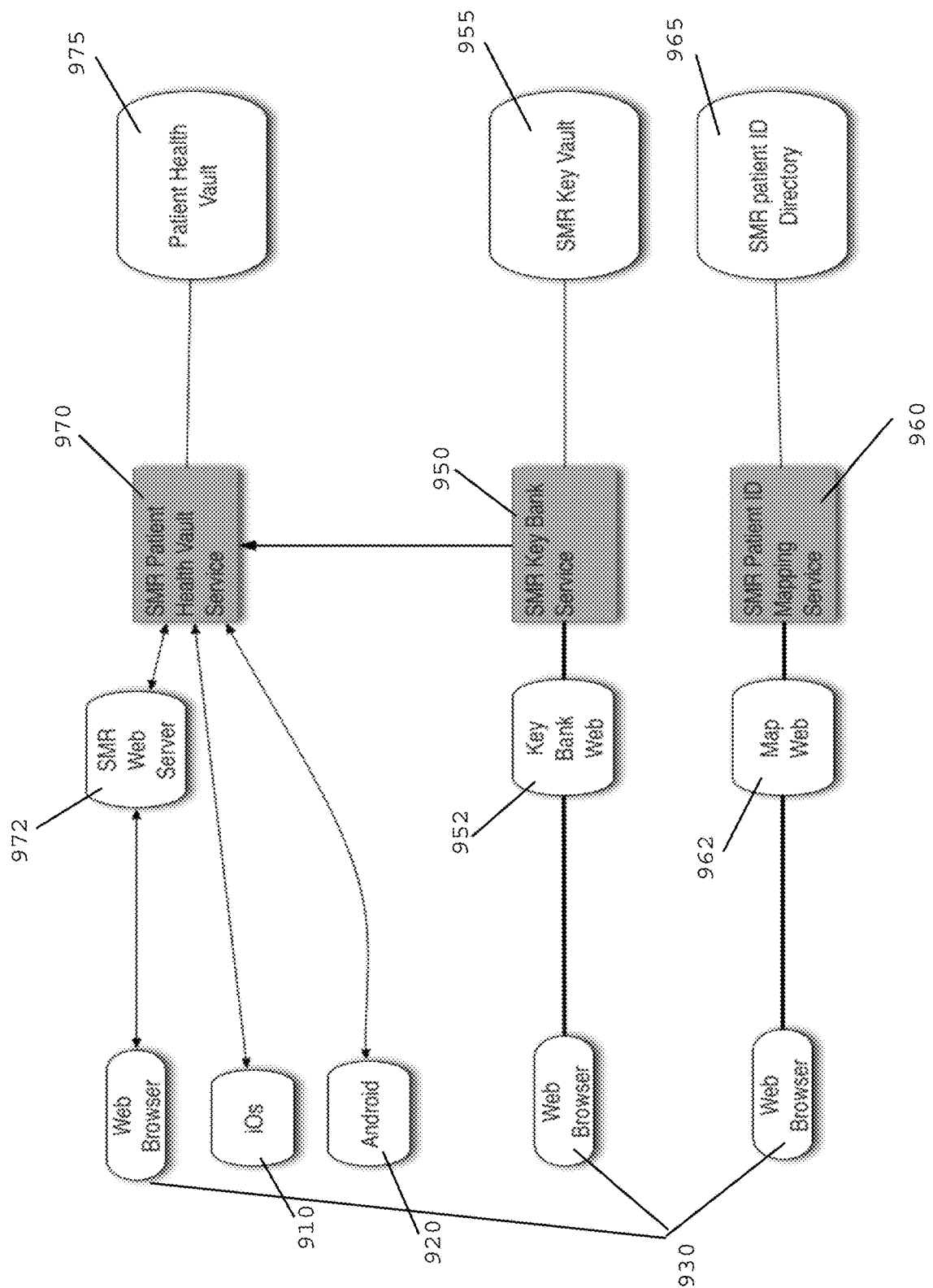
FIG. 9 illustrates a schematic diagram of the access and update of the SMR Patients' Health Vault (PHV) data, together with the use of the Key Bank Service for storing patients' crypto key for access to PHR data in the PHV, and further utilizing the Patient ID Mapping Service for correlating the patient's key and patient authentication data with the account identification for the access to PHV of a particular patient, in accordance with at least one embodiment of the present invention.

The PHV or Data Records Database 160 shown in FIG. 1 may also be split into three different components of the computerized distributed SMR Access system, in accordance with another embodiment or feature of the present invention, as discussed in more details in connection with FIG. 9. Thus, in such an embodiment the SMR system according to the present invention not only keeps the anonymous encrypted PHR data 166 for the patients, but also provides separate Key Bank Server and Secure Directory Mapping Server, as additional security layers of protection to access PHR in the PHV data 166. As further discussed in connection with FIG. 9, the Key Bank Server provides a secure electronic vault for patients that choose to keep a copy of their PHV private symmetric crypto key in the vault, instead of, or in addition to, keeping their keys in their own possession. A properly formatted request with correct verified credentials of the patent will be processed by the Key Bank Server and provide the key directly to the PHV Server 160, or to the patient or patient's authorized device. The PHV Account Directory Mapping Server, as discussed in FIG. 9, after performing authentication of a properly formatted request with the proper patient private crypto key and correct verified credentials of the patient will provide the PHV account number for a given patient will provide the PHV account number (or some account identifier) for a given patient, based at least partially on the private crypto key from the Key Bank Server for a particular patient. Finally, having obtained the proper private crypto key for a patient and account number for a particular patient, the PHV Server 160 will process and verify this data and use the private crypto key of the patient to retrieve and/or update PHV data 166. In such embodiment, the PHV 160 would only be one of three components, and would not store the private crypto key together with PHV data at the same server location. Instead, it would only contain record locator id (or location key) 165 and the actual PHV data 166 in the PHV database. The data stored in PHV for a patient is stripped of any identifiable information and reduced to only an account or location identifier 165 and the encrypted patient's PHR records 166. In such system, even if someone who is not authorized intercepts the decrypted PHV data record when it is being transmitted by the PHV server, this information would be practically useless without correlating it to the proper patient account, which would not be possible without going through the PHV Account Directory Mapping Service/Server 960, as shown in FIG. 9. Thus, it would add yet another level of security for the PHV data access and update capability.

In accordance with the present invention, the PHV 975 and PHV Server 970 do not store or maintain a copy of the patient's private crypto key for access to patient's PHR data in PHV 975. The SMR server 970 will receive the patient's crypto key only for a limited duration, to keep it in RAM for access to PHR data for reading and updates authorized by the patient during limited specified time period, such as for example during patient's visit to HCP's office. Once the authorized access or update processes are completed, the SMR server 970 will erase the patient's crypto key from its RAM. The permanent key of the patient is kept by that patient on his or her electronic device, phone or placed and kept in the Key Bank 950.

In one or more embodiments, the present invention utilizes the computer software or AI to extract and/or organize the patient's medical records stored in the individual HCP's databases and to build a universal or a uniform data organization model in the PHV. The original medical records could be stored in different databases or disparate data sources that have idiosyncratic organization, access or other incompatibilities. They could be difficult to integrate with other data sources of the patient's medical records, and may have technical incompatibilities in connection with obtaining and integrating related information or performing updates on the patient's records. Thus, a common structure data model used by the PHV in connection with present invention allows a uniform organization and reorganization of the data stored in various structured and unstructured HCP data sources into a single structured data that resides in the PHV.

The computer software or AI may be utilized by the present invention, in accordance with various embodiments, to organize disparate medical data records, sort them and re-arrange the data into a structured format that is utilized by the PHV. The computer software or AI may take, for example, the unstructured medical data from multiple sources and populate the PHV with the formatted/re-formatted combined data. This allows the system to have only one universal format and a central location for a full set of patient's medical data for any future updates, changes, etc. In addition, it allows the patient, the patient's representative or the appointed trustee (or a health care proxy or appointed representative for the patient) to permit and allow one or many HCPs and others a uniform and controlled access to the complete set of patient's medical data records that is stored in a structured PHV data source location. Furthermore, it allows the access to be time-limited or the authorization to be directed to the specific HCP. For example, the patient or patient's authorized representative may authorize the hospital that is treating the patient (during the patient's stay or for some duration) to have access to the PHV medical records for the patient, and update the central records with any additional medical data.

In one embodiment of the present invention, the Proximity Detection Server 184 and the computer device (node) 130 in the doctor's or HCP's office preferably communicate via Internet (or possibly through LAN, or connected or distributed network) with HCP Patient Authorization Server 183 and Doctor or HCP Mobile Device Server 182. As part of the communication, the HCP Patient Authorization Server 183 may communicate with the HCP Mobile Device Server to confirm (1) patient's proximity location in the HCP or doctor's office; and (2) whether the patient is there for medical service (and not for some other unrelated purposes).

In another embodiment, the HCP Mobile Device Server 182 and HCP Patient Authorization Server 183 may be located at the same physical location and communicate directly, through the direct wired connection, or could be even be located on the same physical computer server, accessed by the same computer processor.

In addition, or in an alternative embodiment, the identity of each patient operating the patient's mobile devices 110 and 120 may also be confirmed by requesting a digital fingerprint of the person operating the mobile device, receiving this digital fingerprint at the HCP Patient Authorization Server 183 and comparing it with each patient's registration records, to make sure that the right person is operating the patient's mobile device. It also allows patients to use different mobile devices and confirm their identity to the HCP Patient Authorization Server 183 by the transmission of a digital fingerprint extracted by the hardware and app software on the mobile device. The app being executed on the mobile device will require the user to make a digital fingerprint and will transmit it for authentication to the server 183. As discussed, other electronic identification methodology can be used instead of digital fingerprints in accordance with the present invention, including, without limitation, digital facial recognition, retina scans, etc.

In the embodiment where the Data Records Database (or PHV) 160 is split into three separate server components, the patient mobile devices 110 and 120 may also access separately, through the internet router 140 and Internet 150, the Key Vault Server and PHV Account Directory Mapping Server, in order to extract the private crypto key for a patient form the Key Vault, and then map and obtain correct account identification or location id for the patient. Then, the obtained location id (or key) and the private crypto key of the patient are used to located and access patient's PHR stored in the PHV data 166 in the Data Records Database of PHV 160, as discussed above and in connection with FIG. 9.

Figure 16:
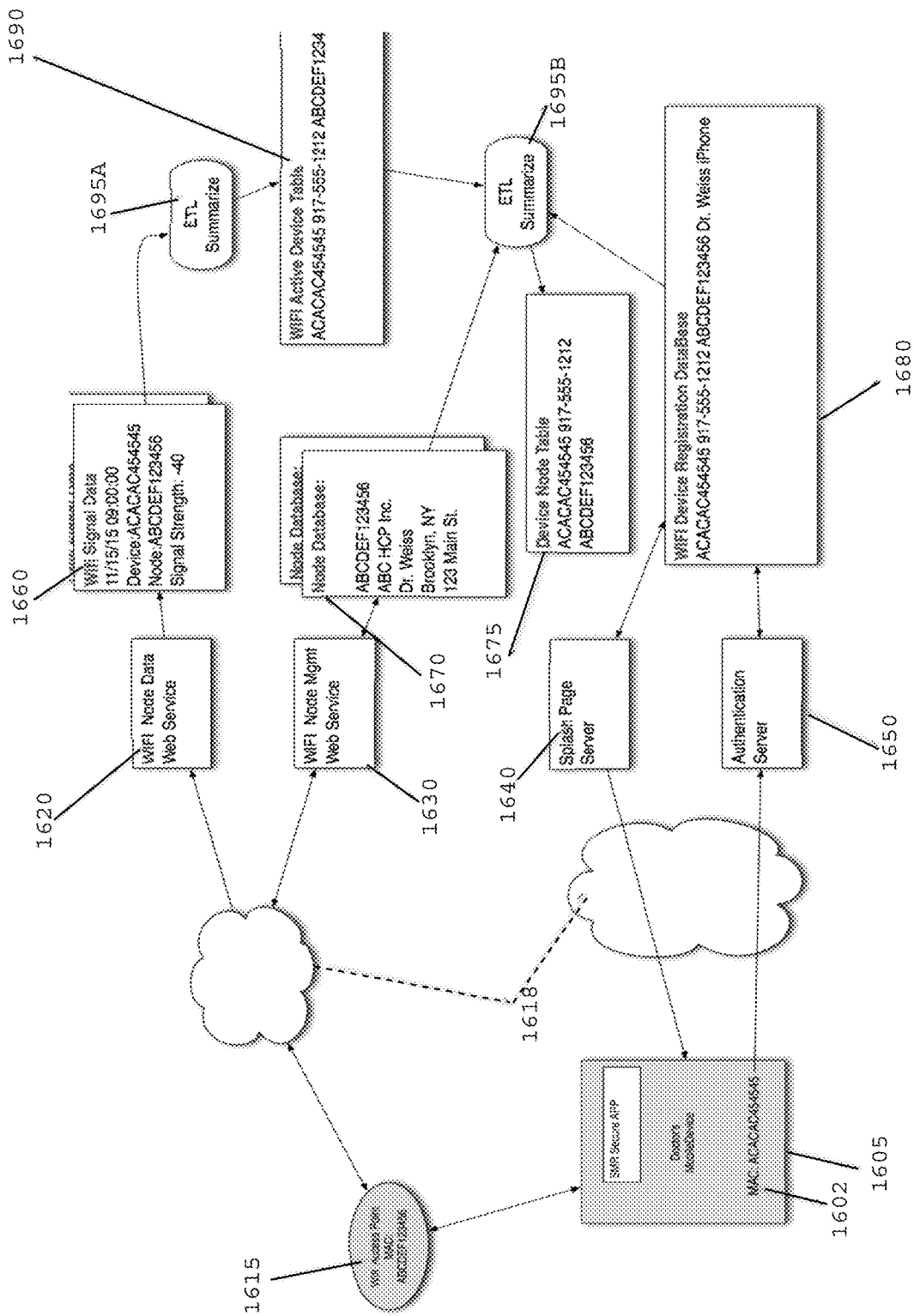
FIG. 16 illustrates a diagram of a cloud architecture and data storage architecture for storing patient's PHR medical records in accordance with at least one other embodiment of the present invention and overall organization of the SMR servers and PHV in accordance with at least one embodiment of the present invention.

Another diagram of a cloud architecture and data storage architecture for storing SMR patient medical records in accordance with at least one embodiment of the present invention is depicted in FIG. 16.

It shows a patient's or doctor's phone or computer device 1605, with MAC address 1602, which identifies the devices. The WiFi node or computer device 1615 determines when the patient's or doctor's phone or computer device 1605 is in proximity of a node 1615. For example, when the patient's or doctor's device is in the same geographic location, the node 1615 determines that it is in its proximity. It communicates this information through the Internet 1618 to the WiFi Node Data Web Server 1620, which records and maintains this information in the Device Proximity Database 1660, which keeps the device information and the strength of the signals for each device that is in the proximity to the node 1615. The WiFi Node Management Web Service 1630 receives information from each WiFi node or computer device 1615 and maintains the node information in the Node Database 1670, which stores and maintains information about each node or proximity-sensing computer device in HCP's office. The 1640—Splash Page Server 1640 communicate with the patient or doctor mobile device (such as sending "Welcome to WiFi webpage") and may ask for the phone number or identification information of the mobile device 1605. For authentication, the mobile device 1605 communicates with the Authentication Server 1650, which stores it in the WiFi Device Registration Database 1680, which keeps data and information about each authorized doctor's and/or patient's mobile device. The mobile device 1605 may also send identification information to the Splash Page Server 1640, which may also populate the WiFi Device Registration Database 1680 with the information of all authenticated and registered mobile devices. In one of the embodiments, the WiFi Device Registration Database 1680 stores only the information about mobile devices of HCPs that are authenticated by the Authentication Server 1650, but in others, it may also store other authenticated device information. In one embodiment, as shown in FIG. 16, the Device Proximity Database 1660 repeatedly and/or periodically stores information about devices in proximity to node 1615, together with a date and time information or timestamp, indicating when the proximity information was sent or received. Thus, it may save data in real-time, with multiple records for the same device, but received at different time. This time-specific data is send to and processed by the ETL Summarize service or module 1695, at which point the duplicate records are removed and currently active mobile devices in proximity to node 1615 are stored in the extract as WiFi Active Device Table 1690. In turn, this information about currently active devices in proximity to node 1615 is sent to another ETL Summarize service or module 1695B, where this information is processed together with data from the WiFi Device Registration Database 1680 about authorized mobile devices and Node Database 1670 about different nodes, to determine and create the Device Node Table 1675, which contains data about all authorized mobile devices of both doctors and patients that are in the proximity of node 1615, or in the proximity of a server or computer with proximity determining capabilities in the HCPs office. The Device Node Table 1675 is the result of the process shown in FIG. 16.

Figure 12:
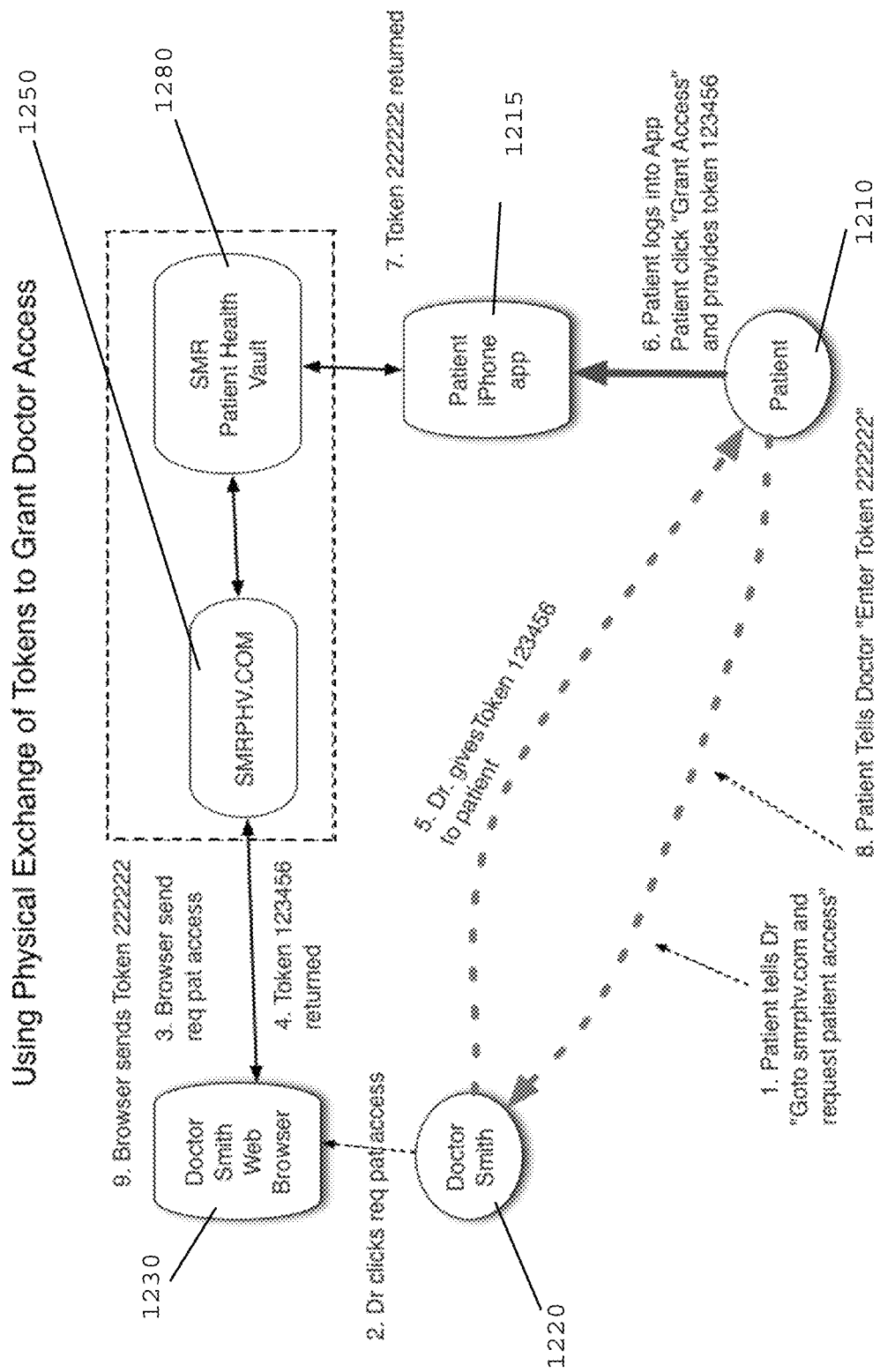
FIG. 12 illustrates a diagram and the process flow of granting access to patient's PHR data by the exchange of tokens in in accordance with at least one embodiment of the present invention.
Figure 13:
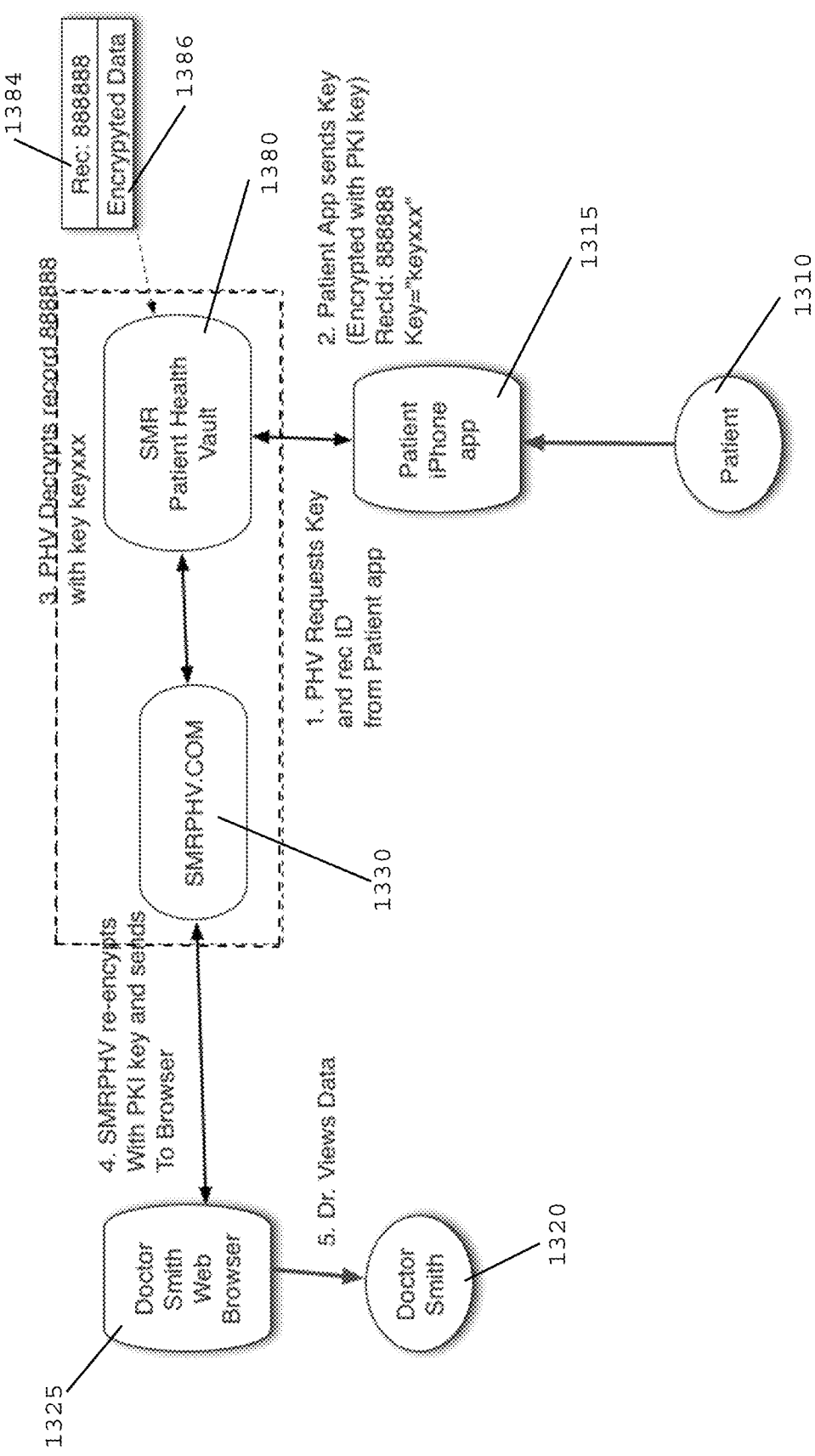
FIG. 13 illustrates a diagram and the process flow of the process to allow the HCP to view the patient's PHR data when the HCP was already granted access by the patient in accordance with at least one embodiment of the present invention.

In addition to proximity location methodology described in connection with FIG. 16, the present system may also request and process digital identification data (for example, digital fingerprints, or other digital identification and recognition data) of the patents and doctors, to confirm the right person is operating the authenticated mobile device that is in proximity to the note 1615. Furthermore, in accordance with another embodiment, the system may also use digital token exchange method for authentication, as shown in FIGS. 12 and 13 and the related description below.

B. Patient's Data Upload and Access to PHR

Referring to FIG. 1, the proximity information about each patient mobile device 110 and 120 is transmitted to and evaluated at the Proximity Detection Server 184 and the doctor's or HCP's mobile device information is received and processed at the HCP Mobile Device Server 182. The HCP Patient Authentication Server 183 communicates with the HCP Mobile device server to process requests to (1) view; and/or (2) update patient data, which the patient grants with secure key access to the a particular HCP based on patient's physical presence at the HCP or doctor's office and key authorization. It may also rely on the digital fingerprint (or other digital authentication, like facial recognition, retina scan, etc.) of the person who is operating the device to assure that the patient has granted access and that the authorized HCP is operating the mobile device that has requested access to the patient's PHR.

The patient can grant access and/or update to his medical data through the following settings, and subject to the following limitations set by the patient:
  (1) full access to a particular doctor or HCP;
  (2) full access, but only during the period of time when patient's device (operated by the patient) is physically present at the HCP or doctor's office;
  (3) full access, after the authentication and proximity verification, for a specific but limited time period.

The latter setting (3) would be preferable when a patient intends to allow access to his or her medical data during and after a visit, and for one or more hours (or possibly days) following either the start or completion of the visit and examination. This would allow the HCP or doctor to make updates and changes to the medical data immediately following a patient's visit, but would prevent indefinite access and continued responsibility for the data access and security of patient's data.

Figure 2:
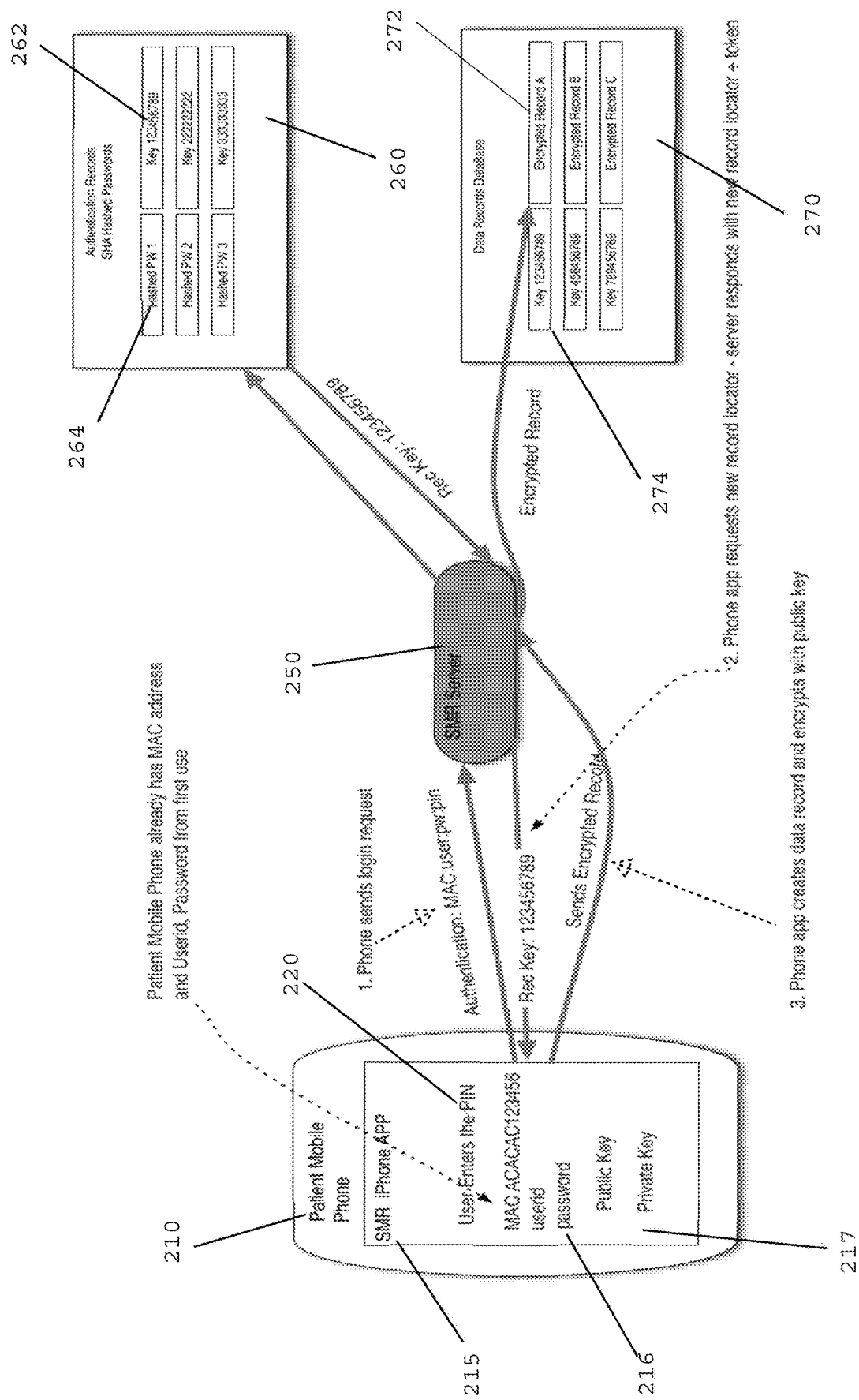
FIG. 2 illustrates a diagram and the process flow chart of a patient medical records upload process for storing patient records in accordance with at least one embodiment of the present invention.
Figure 3:
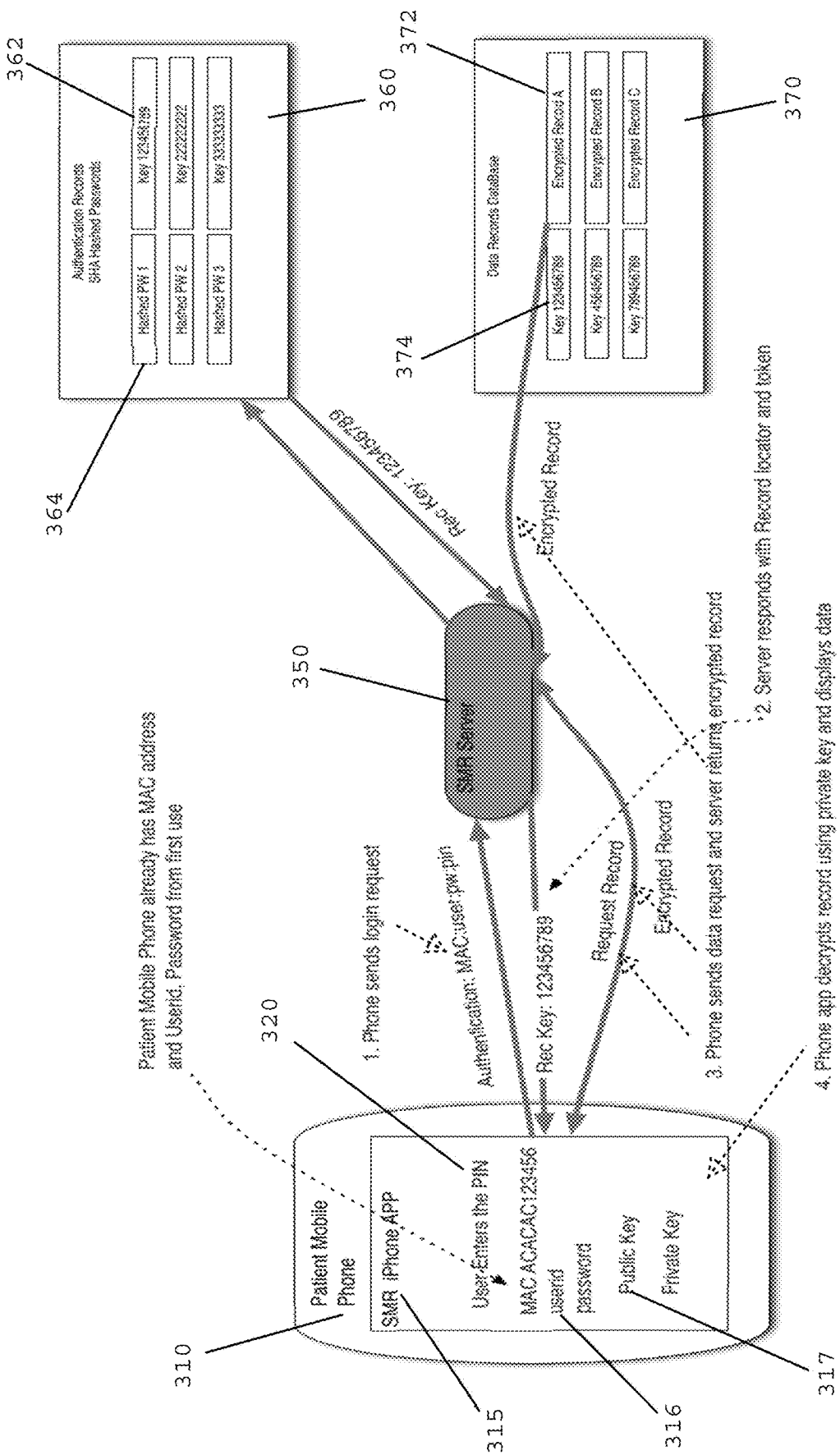
FIG. 3 illustrates a diagram and the process flow chart of a patient's access to data uploaded and stored in the SMR system in accordance with at least one embodiment of the present invention.

The further process of uploading of patients' data is described with reference to FIG. 2, and patient access to PHR is described with reference to FIG. 3. Patient data records can be stored in one central database or store or in a distributed database(s) or store. In either case one or more Web-based services and servers provide access to the correct records based on requests from authenticated clients. As depicted in FIGS. 2 and 3, a single web server called the "SMR Server," 250 and 350, respectively, receives requests from patients mobile phones, 210 and 310, processes and authenticates the requests through an SMR smart phone app, depicted as SMR iPhone App 215 and 315. The present SMR system preferably utilizes a PKI Asymmetric key encryption methodology and architecture for secure transmission of data and communications. The SMR Server has at least one processor and RAM or other memory for storing and processing computer instructions and for temporary storage of the received requests and information from the mobile devices.

In the PKI Asymmetric key architecture, there is a pair of two keys—public and private. The first key can be used to encrypt data. Once data is encrypted with the first key, it can only be decrypted with the second key. Typically, the first key is called the "public key" and the second is the "private key" and the use of public-private key combination is referred to as Asymmetric crypto key process or PKI Asymmetric key architecture, which is used for the secure transmission and communications with the server. In the PKI Asymmetric key architecture, the transmitted data can be encrypted with the public key but cannot be decrypted with that public key. The encrypted data can only be decrypted by the private key.

In the Symmetric Key Architecture, the same key or key components are used for encryption and decryption of the data encoded using the Symmetric Key. Thus, it applies to the regular private key architecture, where one key is typically used for both encryption and decryption. Thus, transmission of this symmetric key is required in order to effectively encrypt or decrypt PHR patient's data using patient's Symmetric Key, in accordance with at least one embodiment of the present invention. The patient provides and transmits his Symmetric Key to the SMR server and PHV for a limited time, to allow a particular authorized HCP or doctor to gain access to the patient's encrypted PHR in the PHV. This patient's private crypto key is not sent or maintained by the doctor or HCP, and the patient needs only one key to allow multiple HCPs to read and update patients PHR that is centrally stored in encrypted format in the PHV.

In the present SMR system, the private and public keys and private crypto key may be stored in the patient mobile device (or computer) 210 and 310, having a processor and computer memory for executing computer instructions on the mobile device and for storing data in RAM or other memory on the device. As discussed above and below, with reference to FIG. 9, the patients' private crypto keys may also be stored on the SMR Key Vault Server, and accessed only by the patient or authorized person using some private patient information and/or authorized patient device. As part of this authorization, the system may also require transmission of the digital fingerprint (or other digital authentication, like facial recognition, retina scan, etc.) of the person operating the mobile device, to make sure that it is actually patient himself or herself (or their authorized representative) or the authorized HCP is requesting access from the HCP's mobile device or computer or permitting access to the PHR data from the patient's mobile device or computer. The fingerprint authorization technology (or other digital authentication, like facial recognition, retina scan, etc.) also allows patients and HCPs to switch mobile devices or computers, without the need to redo the full authorization process with each new device, or to use someone else's mobile device or computer for authorization and PHV data access.

In one embodiment, the patient enters data on his mobile device. In most cases, it may not be the patient entering the data himself or herself, but they can do so themselves. The system is designed to allow the doctor to add and update records for the patient. But, at least one of the embodiments of the present invention contemplates that the patient information may be entered by the patient, or someone next to the patient, on the patient's own mobile device 210 and 310, possibly using a touch screen or keyboard. The application software processed by a computer processor on the mobile device provides a facility for the patient user to generate a pair of public and private keys. The process is similar to the way the "bit Wallet" for Bit Coin applications work. The bit Wallet application is used to manage Bit Coins. In the present SMR system, the user creates a folder and then creates "addresses" within the folder. For each patient folder, the app will generate a public and private key pairs 217 and 317, which are stored on the patient's mobile device 210 and 310. The patient's private crypto key may also be stored in the computer memory of the mobile device 210 and/or placed and stored in the SMR Key Vault Database (if this additional service is chosen by the patient).

Once a folder is created, the user can "upload" that data to the cloud. When the user uploads that data, the data is encrypted with the private crypto key of the patient and sent to the SMR Server 250 and 350. The transmission may further use Asymmetric PKI key encryption methodology to secure and encrypt all transmissions between the patient's mobile device 210 and 310 and the SMR Server 250 and 350. As discussed, the databases are preferably cloud-based distributed databases, but can also be the conventional SQL or other relational, hierarchical, network-based or flat record databases or electronic record storing systems. The SMR Server 250 and 350 preferably returns a 7-digit record location number or key back to the mobile device. The app stores this record locator on the device.

The Patient Data Upload process is shown with reference to FIG. 2. As Step 1, the software application 215 running and executed by a processor on the Patient Mobile Phone 210 sends a login request to the SMR Server 250. In one embodiment, the authentication request may include and transmit such information as the MAC address of the smart phone 210 and the userid, password and pin of the user of the smart phone 210. Once authenticated, the phone app then requests the record locator id or key for the patient. The Authentication Database or Authentication Records SHA Hashed Passwords Table 260 may store the hashed MAC, user id, password and pin information sent in Step 1 as Hashed PW 264 in the Authentication Database 260. As shown in Step 2, the SMR Server 250 returns back to the mobile device the record location id or key Rec Key 262, which represents the record locator for the encrypted PHR records of the particular patient, stored as encrypted records A, B, C 272 in the Data Records Database (PHV) 270. The record location id or Rec Keys 262 and 274 help identify and locate the PHR records of a particular patient that are stored in the encrypted format, encrypted with that patient's private crypto key, in the Data Records Database (PHV) 270. In simple terms, the record location id indicates the electronic room number of the stored PHR for a patient. If this is a first upload of the patient's PHR data into the Data Records Database 270, the record location id or Rec Key returned to the device 210 will indicate the actual record location or record location id 274 to which the PHR data is to be stored and uploaded. As Step 3, the phone application 215 running by a processor on the mobile device 210 encrypts the data record with patient's private crypto key (symmetric key) and sends it for the transmission to the SMR Server 250 for storage in Data Record Database 270 as Encrypted Records A, B and C 272. While the actual PHR data records are encrypted with patient's private crypto key, the transmission may also encrypt all transmitted data using Asymmetric public key of the server, to protect all communications between the device 210 and server. Thus, in accordance with at least one embodiment, the transmission of the PHR data records may utilize multiple levels of encryption for additional security: (1) encryption of the PHR underlying records with the symmetric private key of the patient; and (2) encryption with the public key of the server for transmission to the SMR Server, used for secure transmissions. The encryption strategy utilized in accordance with the present invention is further shown and described in connection with FIG. 15 and FIG. 7.

Referring to FIGS. 2 and 3, to authenticate the login request, at the SMR Server, the user mobile device app 215 and 315 may send to the SMR Server the MAC address of the device and a userid and password, shown as 216, 217 and 316, 317. Where the device, such as Apple iOs App cannot access the local MAC address, it may utilize the process described later in this specification, to obtain the MAC address by having it detected by a "Wifi Node" and made securely available to the App 215 and 315 by the SMR Server 250 and 350.

Once the user is authenticated, still no data can be transferred without requesting a particular record identified with the 7-digit record locator id or Rec Key shown as 262 and 362. The record locator id ok Rec Key for each patient is also stored in the Data Records Database 270 and 370 as record locator key 274 and 374 in FIGS. 2 and 3, respectively. For the patient that owns this data and has his mobile device—this entire process is transparent, since all of the keys and passwords are stored and secured by the device using the security mechanism and App on the smart phone device.

In a preferred embodiment, the user is still required to enter a 4-digit pin, depicted as step 220 and 320 on FIGS. 2 and 3. The pin is preferably entered on each use, so that even if the phone is stolen and hacked, the PHR data on the cloud cannot be accessed. However, this feature is optional. The user may decide on the trade-off between the ease of use and security for his or her PHR data.

FIG. 3 illustrates the Patient Data Retrieval Process for the retrieval of PHR data from the PHV in accordance with at least one embodiment of the present invention. As Step 1, the software application 315 running and executed by a processor on the Patient Mobile Phone 310 sends a login request to the SMR Server 350. In one embodiment, the authentication request may include and transmit such information as the MAC address of the smart phone 310 and the userid, password and pin of the user of the smart phone 310. Once authenticated, the phone app then requests the record location id (or location key) for the patient. The Authentication Database or Authentication Records SHA Hashed Passwords Table 360 may store the hashed MAC, user id, password and pin information sent in Step 1 as Hashed PW 364 in the Authentication Database 360. As shown in Step 2 in FIG. 3, the SMR Server 350 returns back to the mobile device the record location id (or location key) Rec Key 362, which represents the record locator for the encrypted PHR records of the particular patient, stored as encrypted records A, B, C 372 in the Data Records Database (PHV) 270. The record location id or Rec Keys 362 and 374 help identify and locate the PHR records of a particular patient that are stored in the encrypted format, encrypted with that patient's private crypto key, in the Data Records Database (PHV) 370. As Step 3, the phone application 315 running by a processor on the mobile device 310 requests return of the encrypted PHR data for the patient from the SMR Server 350. The SMR Server 350 utilizes the record location id (or location key) 362 and 374 to locate the PHR data for the specific patient and sends back the encrypted PHR records 372 for that patient back to the mobile device 310. As Step 4, the patient's app 310 and the processor execute code to decrypt the received PHR data records from the SMR Server 350 and then utilize the patient's private crypto key to decrypt and display the decrypted PHR records on the patient's mobile phone 310. Alternatively, the SMR Server may decrypt the PHR record extracted from the PHV 362 using patient's private symmetric crypto key at the SMR server 350, and then transmit it back to the patient re-encrypted with server's asymmetric PKI key. In this case, the server would also send to the patient's app 315 the server asymmetric PKI key that allows patient to decrypt the transmitted and re-encrypted PHR records. Alternatively, the SMR server 350 may decrypt the PHR using patient's private crypto key at the server, and then re-encrypt it for transmission using patient's asymmetric PKI public key, which the patient's app sends to the server. In this case, the re-encrypted PHR is sent from the server 350 to the patient device, where it can be decrypted using patient's asymmetric PKI private key. Thus, the decryption of the PHR records from the PHV can be done either on the SMR server 350, or on the patient's mobile device, in accordance with different embodiments of the present invention.

It should be understood that any number of digits may be used for the locator numbers, account numbers, ids, pins or keys in accordance with at least one of the embodiments of the present invention.

C. Key Encryption and Decryption

The key encryption strategy and general encryption scheme that may be utilized by the present invention is described with reference to FIG. 15. The transmission protocol utilizes PKI Asymmetric key encryption transmission for secure transmissions, but the patient and server use patient's private Symmetric key for encrypting and decrypting the PHR data of the patient, including the updates to stored records. The patient mobile device 1510 establishes secure communication with SMR Services Server 1550. The patient mobile device 1510 receives SMR Services Server(s) public key and encrypts patient's private symmetric key using the server's public key, which is sent to the patient mobile device by the SMR Server 1550. The SMR Server 1550 receives the symmetric private key of the patient from the patient mobile device 1510 and uses server's private key to decrypt the transmission. The patient must also give a separate authorization for a particular doctor or HCP to have the permission to use the patient's symmetric private key for decrypting and reading or updating the PHR of that patient on the SMR Server 1550. This allows the SMR Server(s) 1550 to encrypt and decrypt the data in the PHV for the duration of the authorized access for a particular doctor or HCP, as authorized by the patent. Once the authorization expires, the SMR Server 1550 would erase the private symmetric key of the patient, and not keep it in any of its internal memory or PHV database.

The SMR Services Server 1550 also communicates with HCP or doctor's mobile device 1520 and Patient Health Vault (PHV) Server and Data 1530, which stores encrypted patient medical records. When SMR Serer 1550 confirms that a particular authorized doctor is permitted to read or update the PHR of the patient using mobile device 510, it decrypts the PHR of the patient using the patient's private symmetric key, which is received and kept at the SMR Server for the duration of authorized access. It then uses the PKI Asymmetric key of the doctor to re-encrypt the PHR data for secure transmission to the HCP's mobile device 1520.

The doctor's (HCP's) mobile device 1520 receives SMR Server's public key and uses it to encrypt and transmit doctor's public key to the SMR Server 1550. Then, SMR Server 1550 uses doctor's public key to re-encrypt and transmit patient data records from the SMR Server 15530 to the doctor's mobile device 1520, which receives patient records and displays them on the screen of the doctor's mobile device. In this embodiment, the doctor's device does not need to have the patient's private crypto key because this key is sent to the SMR Server 1550, and, when authorized, is used during the authorized session or time period to decrypt PHR data of the patient. The server then re-encrypts the decrypted patient's PHR with doctor's Asymmetric key for secure transmission to the doctor's mobile device from the server. This allows the doctor mobile device 1520 to utilize its public and private keys to decrypt the re-encrypted patient's data and view or update it on the doctor's mobile device. For the updates, the SMR Server will send its public key to the doctor's mobile device 1520, which can be used for encryption of the transmitted updated data. Then, on the SMR server, the updated records will be re-encrypted using the patient private symmetric crypto key, and then stored in the encrypted form in the PHV, with the location id (or key) that identifies the patient and patient's PHR records.

Figure 15:
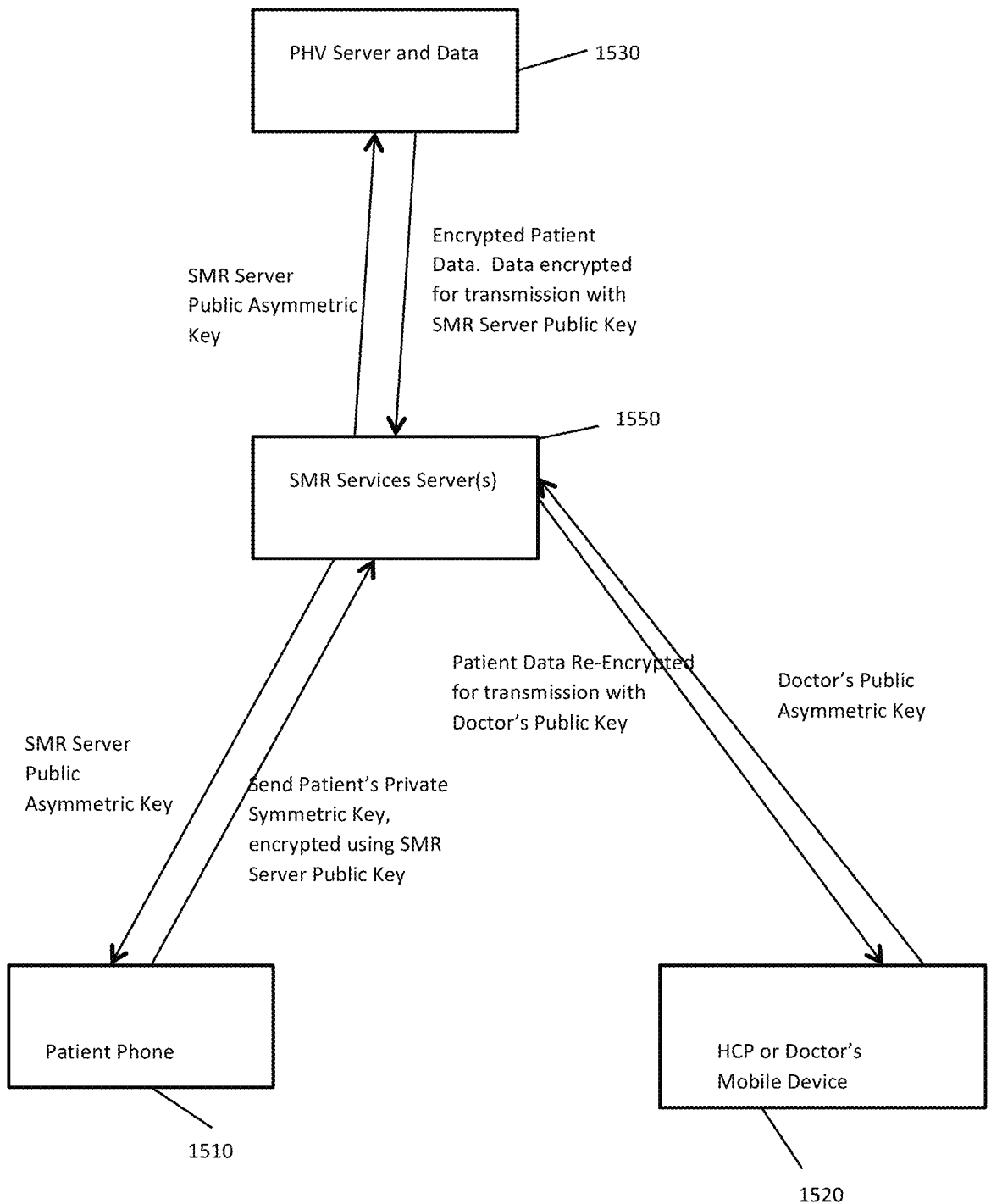
FIG. 15 illustrates a diagram and the process flow of the encryption and decryption strategy utilized during various transmissions between patient's and HCP's mobile devices, Private Health Vault Server and Data storage or database and the SMR Services Server(s) in accordance with at least one embodiment of the present invention.

It should be noted that communications and transmissions of information shown on FIG. 15 may proceed through the Internet or possibly though the local area or distributed network, or a combination of both, and that each transmission (shown by arrow) may proceed through one or more other servers, hubs of intermediate computer devices, ISP servers, modems, firewalls or other known Internet access enabling components.

Referring back to FIGS. 2 and 3, after authentication is done and the SMR Servers 250 and 350 are provided the new record location id (location key) 262 and 362 and 274 and 374 for use with patient's data record, the smart phone creates a data record and encrypts it with a record number and patient's private symmetric key. The encrypted patient data records 272 and 372 are preferably stored in a separate Data Records Database 270 and 370, together with location id (location key) 274 and 374 used for the identification and location of the patient's records.

Referring to FIG. 3, after the authentication of the patient's device, the phone App 315 on the patient's phone sends a data request to SMR Server 350. The request and the userid and passwords from the patient are processed by the processor on the SMR Server, which then automatically generates a request to the Authentication Records Database 360 and receives the record location id (location key) 362 and 374 used for the location of patient's data records. This location key is then sent to the Data Records Database, which uses the key to find and return to SMR Server the encrypted PHR data records 370 for that patient. The encrypted PHR records are transmitted to the SMR Server and then to the patient's mobile device 310. Any losses of data during this transfer process, or even the loss of the encryption key do not impact the data security for the PHR because these encrypted data records can't be decrypted and read without the patient's "private" key, which is not sent for data retrieval or upload from the patient's device. Furthermore, even if the Data Records Database is hacked and data records stolen, the data can't be decrypted without each patient's private crypto key, which is different for each patient.

D. Providing Access to Data for Doctor and/or HCP

In at least one embodiment of the present invention, the process of access to data by Doctor and/or HCP utilizes a mobile phone or computer device, having a memory and process, and Indoor Location Technology. It is understood that the specific implementation and other types of mobile devices, communication protocols and location technology may be used with the present invention, and that a person skilled in the art may implement those technologies based on the present description without any undue experimentation.

The Indoor Location Technology used with the present invention may use BLE, iBeacon, Bluetooth as well as LED lighting, ultrasound, IR, RF and other technologies for associating and tracking of a mobile device within a particular indoor location. The process is comprised of the following key phases described in more detail below:

1. Doctor/HCP Installs and configures Indoor Location (WiFi) infrastructure
2. Doctor Registers mobile device
3. Patient Registers mobile device
4. Patient authenticates Doctor
5. Patient provides authorization to Doctor to view/update Patient Record
6. Doctor views and Updates patient records An important feature of the above process is that the access that the patient provides to the doctor or HCP is NOT permanent. While the patient may authorize the doctor or HCP to copy the PHR data of the patient to their own EMR system, the doctor or HCP does not maintain and control access to the original electronic version of the patient's PHR data from which a full or partial copy was made by the doctor or HCP. Thus, the doctor or HCP controls/owns and is responsible for his copy of the PHR data and the patient owns and controls his original electronic records. In fact, the patient is the only one that owns and controls access to his complete comprehensive medical records across all HCPs and doctors that treat that patient.

The steps of providing access for doctor or HCP is described in more details below, with reference to FIGS. 4 through 7.

Step 1: Doctor or HCP Installs and Configures Wifi Infrastructure

This installation and configuration step is typically done once for each physical HCP location or doctor's office. The WiFi networks and installation of those networks is well known and commonly used in the HCPs and doctors' offices. The use of this known technology for the purpose of authenticating doctors and patients to the SMR system and for access to PMR data is the novel use of the existing and well known WiFi networks. As part of the configuration process, the doctor may use the hardware and software app on his mobile device to generate and send his digital fingerprint (or other digital authentication, like facial recognition, retina scan, etc.) to the server, which is used later for confirmation that the same doctor is using the mobile device for access to patient's PHR.

Figure 4:
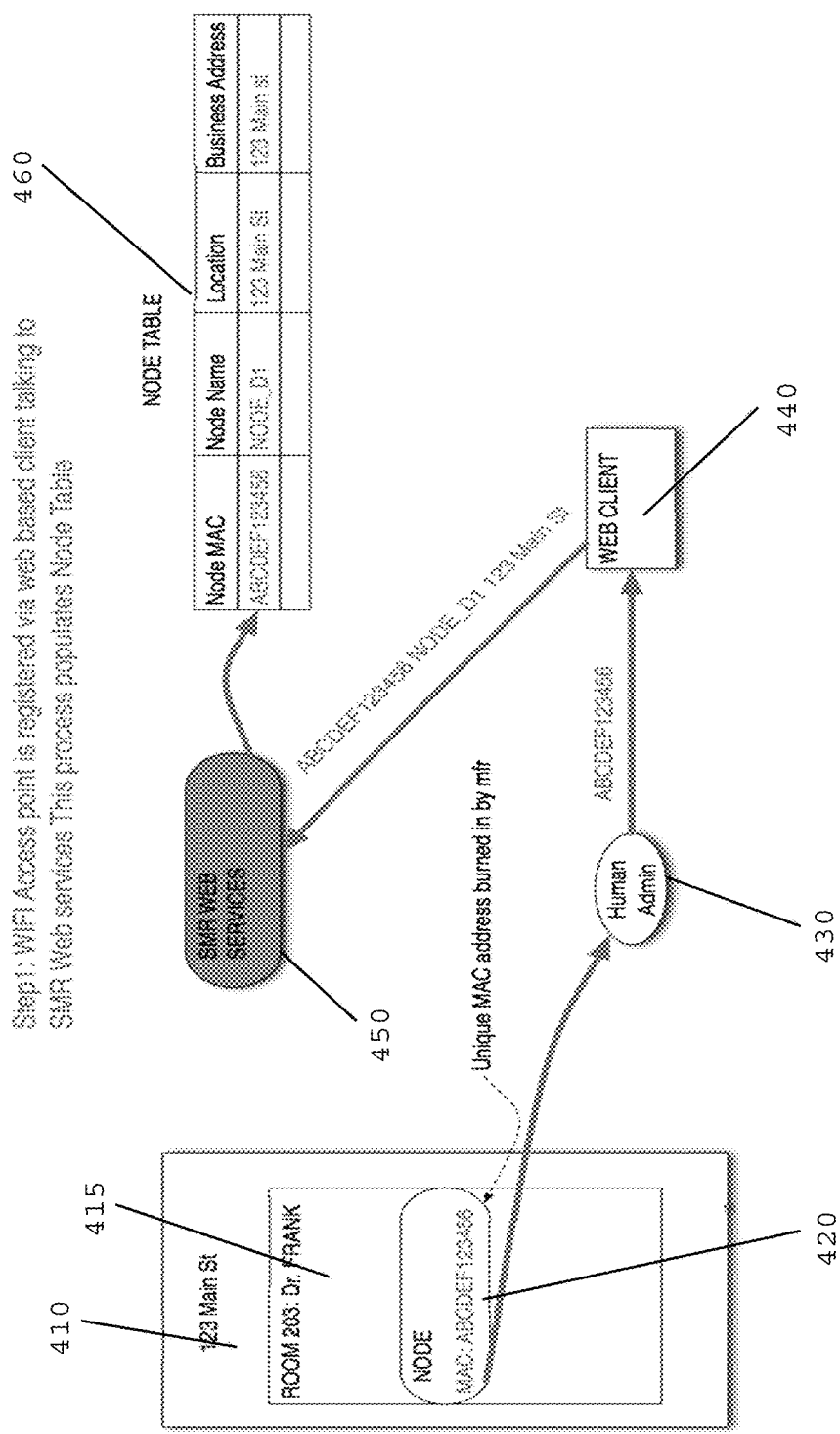
FIG. 4 illustrates a diagram and the process flow chart of the Installation and Configuration of WiFi Node Infrastructure at the HCP's office in accordance with at least one embodiment of the present invention.

Referring to FIG. 4, a typical HCP office 410 typically has a wired or wireless Internet connection and a router. This is a standard feature of every HCP and all kinds of ISP's and routers may be utilized for this functionality. In addition to the existing Internet connection and any existing wifi—the Doctor/HCP office installs in their office one or more Wifi access points referenced in FIG. 4 as one or more Nodes 420. The node may be unique to a particular room 415 or office of a particular doctor in a multi-physician facilities or a hospital. The Nodes are connected to the HCP Internet router and are used for two purposes:

Provide WiFi (typically open and free) to computers and mobile devices in the office Detect the presence and proximity of any devices to the Nodes and report that information back to central secure SMR Server and real-time Node database.

Each Node 420 comes from the manufacturer with a unique ID, which can be the MAC address. The installation of the Nodes involves physically placing them in the HCP offices and then registering the MAC addresses with the central SMR Server (SMR Access, Inc.) and Node database. As shown in FIG. 4, an administrator 430 at the doctor's or HCP's facilities reads the MAC address from the physical device, and sends it through the Web Client 440 and the Internet to the SMR Server 450, where the processor executes computer code to process and update the Central Node database or table in the database 460 with the details about that Node including where the Node is physically located and the name of the HCP, doctor name, and some other identifier of HCP. In at least one embodiment, the Node location indicates its geographical indoor location.

Step 2: Registration of HCP's Mobile Device and Active Device Authorization

Figure 5:
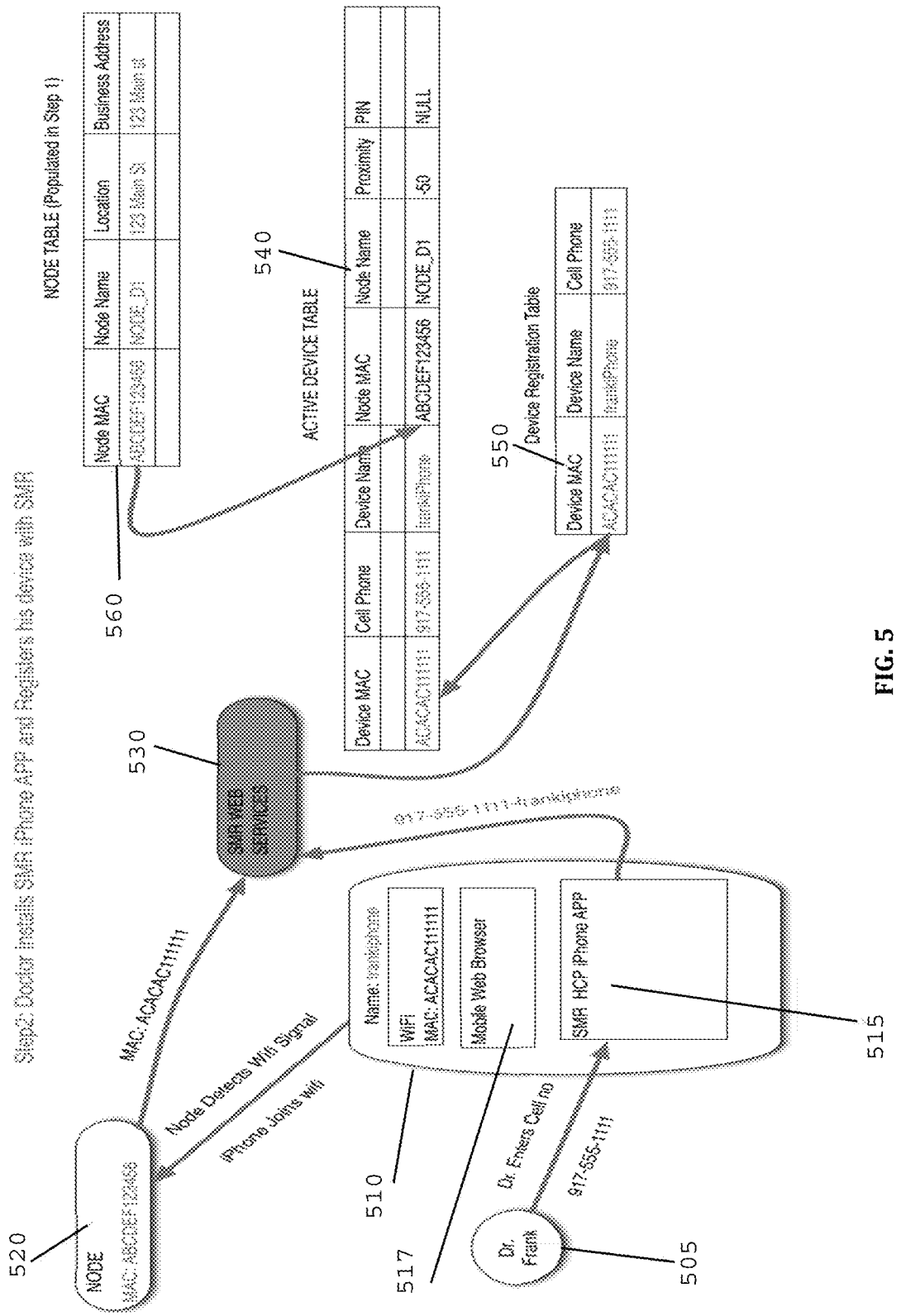
FIG. 5 illustrates a diagram and the process flow chart of the Registration of HCP's mobile device and organization of the proximity detecting node at the HCP's office in accordance with at least one embodiment of the present invention.

The next step is for the Doctor or HCP to register the mobile device with SMR Server. FIG. 5 illustrates the diagram and a flow chart for the registration of a single doctor's mobile device in accordance with at least one embodiment of the present invention. It is understood that in the actual medical office or HCP facilities, the mobile and stationary devices of multiple doctors and staff would be registered with SMR in accordance with the present invention.

This step registers the doctor in the system—so that the system can detect the presence of the patient's mobile device at the doctor's office, and the patient will be able positively identify the doctor's device as being the one authorized to view/update patient medical records in later steps.

Referring to FIG. 5, the HCP 505 downloads and installs the HCP's version of the mobile device App 515 on the HCP's mobile device 510—or set's "doctor mode" or "HCP mode" in the SMR App. The mobile device App requests the cell phone number from the user. In at least one embodiment of the present invention, is necessary for the HCP to enter the mobile/cell phone number of this device because some mobile devices do not allow the cell phone number to be obtained by the App directly from the phone.

The App obtains the configured name of the device—which was typically set when the smart phone, like iPhone, was initially installed and configured. In an iPhone this can be changed by going into settings. This identifier is also used as part of the identification process. The App stores the cell phone number in the App data store—so this only happens once during initial install of the App.

When the mobile device 510 is in proximity of the Node 520 (configured in step 1), the device App takes the entered cell phone number and preferably device name, and automatically connects through the mobile Web Brower 517 and through the Internet to the SMR Server 530 in the cloud, which maintains a database or "in memory table" of active devices or Active Device Table 540 that are currently detected in proximity to a registered node. As shown in FIG. 5, the SMR Server performs a lookup for a particular HCP's device that it is processing in the Device Registration Table 550, and also updates the Active Device Table 540 when the device is in the proximity to Node 520. The database or a Node Table 560 is also maintained by the SMR Server, and looks up the specific Node during the processing of this step. In the example shown in FIG. 5, the resulting Active Device Table 540 is populated with the information about active devices that are also properly registered and authenticated, and are located in the proximity of the Node 520.

Because the Active Device Table 540 contains information about doctor's devices being in the proximity of the Node 520 and patient's mobile device (not shown), this information can also be used monitor and track doctor's activities, length of the procedure and other in formation related to the treatment by the doctor and time spend on any particular activities related to a particular patient. It can also be used for tracking and mapping HCPs movement, patient treatments and other activities.

Step 3: Patient Registration

Figure 6:
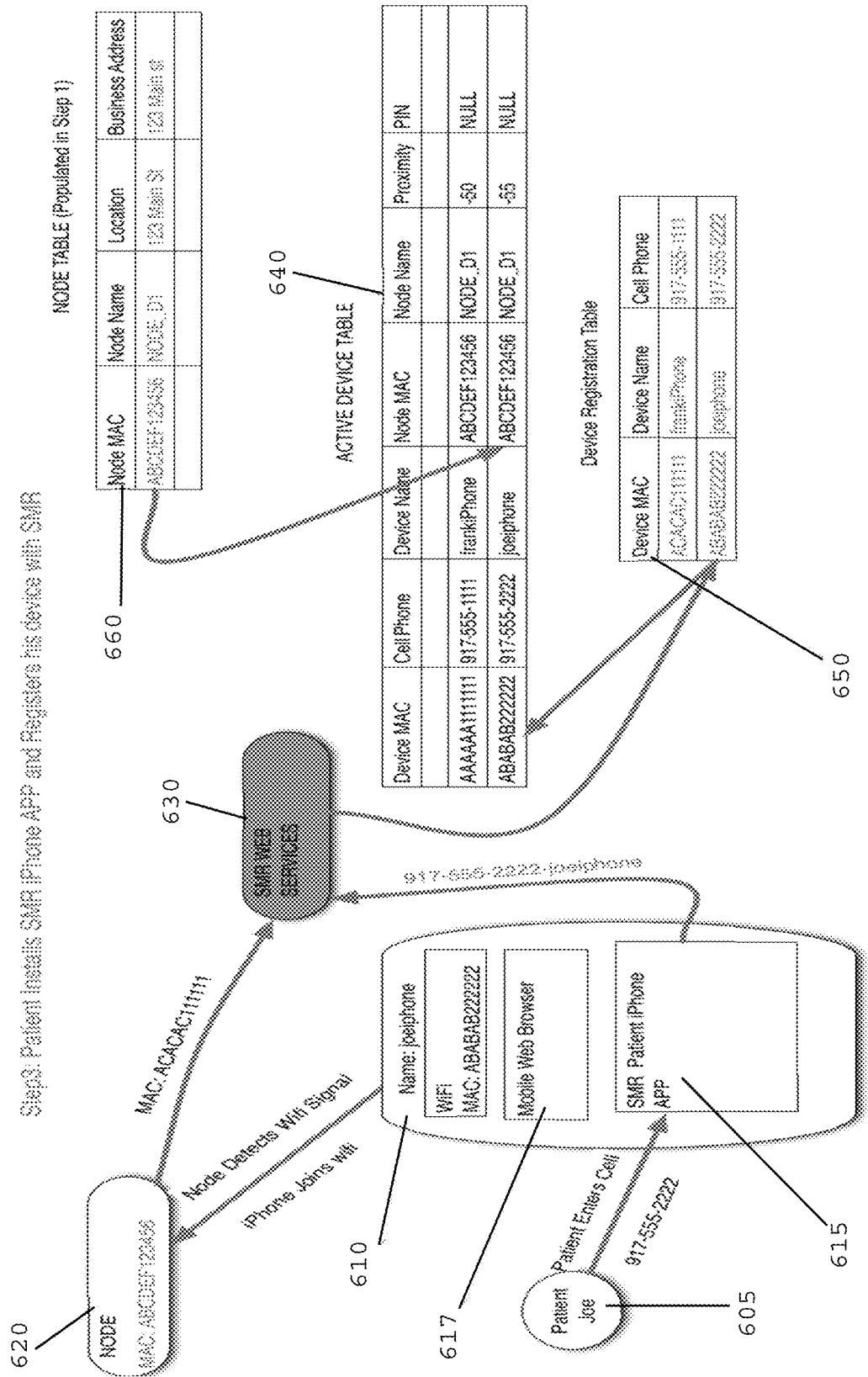
FIG. 6 illustrates a diagram and the process flow of the registration and installation of the SMR services on the patient mobile or computer device in accordance with at least one embodiment of the present invention.

One of ways that the SMR system operates and provides patient authenticating capabilities to the PHR data, and provides access is by electronically determining that both the Patient and HCP are both in the proximity of the known "WiFi Node," shown as 520 and 620 in FIGS. 5 and 6, respectively. Referring to FIG. 6, the registration of the patient's mobile device 610 operates in a similar fashion as the registration of the doctor's or HCP's mobile device described above with reference to FIG. 5.

The patient 605 downloads and installs the device App 615 on the patient's mobile device 610, and provides the patient's mobile device number in response to the App request. The App obtains the configured name of the device. When the patient mobile device 610 is in proximity of the Node 620 (configured in step 1), the device App takes the entered cell phone number and device name, and automatically connects through the mobile Web Brower 617 and through the Internet to the SMR Server 630 in the cloud, which maintains a database or "in memory table" of active devices 640 that are currently detected in proximity to a registered node. The SMR Server then performs a lookup for a particular patient's device that it is processing in the Device Registration Table 650, and also updates the "in memory table" of active devices or Active Device Table 640 when the patient device is in the proximity to Node 620. The SMR also maintains and updates the database or a Node Table 660, and looks up the specific Node during the processing of this step. The Active Device Table 640 includes information for all patients' and all doctors' (registered) mobile devices that are in the proximity of the Node 620, and therefore in general proximity to each other.

When the node 520 and 620 in FIGS. 5 and 6 detects the presence of the doctor's and the patient's mobile devices, the WiFi node automatically connects to the SMR Server and creates Active Device Table 540 and 640, which is populated with the information of active HCP's and patients' mobile devices or computer. This table is used in step 4 below, as the patient provides a certificate for doctor's access to the patients PHR data. The Active Device Table contains "Proximity" data, which indicates the physical proximity of the mobile device entry to the proximity node at a particular HCP location. This Proximity data (shown in the Active Device Table 640 in FIG. 6 under the Proximity Heading) may be derived or based on the signal strength or some other known position determining methods, such as RF, US or IR or other, based on the signal triangulation and position determination based on signal strength and travel delay.

Step 4: Patient Validates and Authorizes Doctor to Access PHR Data

Figure 7:
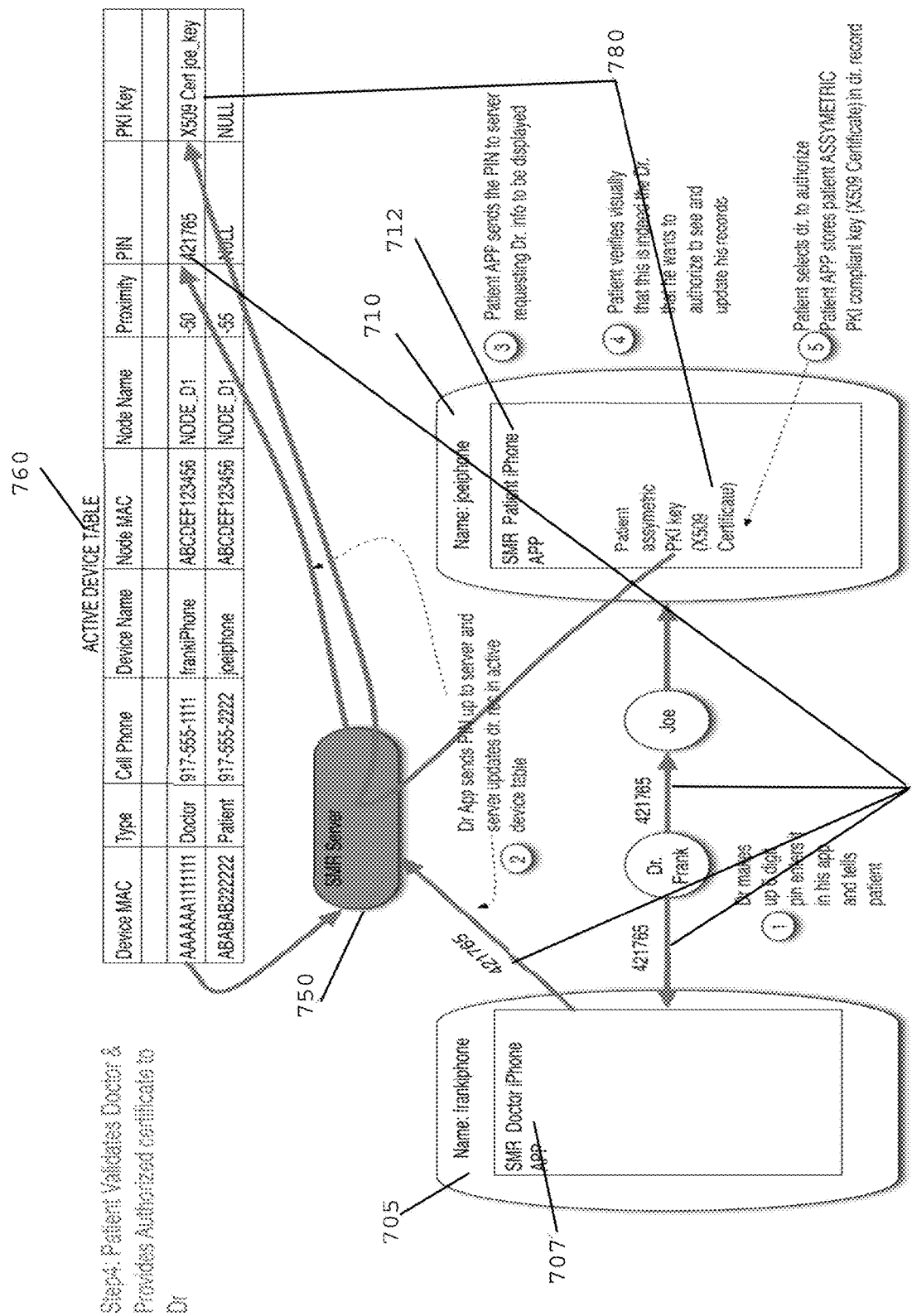
FIG. 7 illustrates a diagram and the process flow of the patient's validation and authorization of the HCP for access to the patient's PHR data on the SMR server and system in accordance with at least one embodiment of the present invention.

Referring to FIG. 7, once the SMR system determines that both the Patient's and Doctor's (or HCP's) mobile devices, 705 and 710, respectively, are in the proximity of the WiFi Node (not shown), the SMR Server 750 updates the Active Device Table or database 760 to include records for both the Doctor's and Patient's mobile devices. The validation and authorization process proceeds as follows:

(1) Doctor makes up a 6-digit PIN 709 and enters it in his SMR Doctor Phone App 707. Alternatively, the server 750 may create a PIN for the doctor and sends to the doctor (encrypted), for the doctor's use.

(2) Doctor Phone App 707 transmits the entered PIN through the Mobile Web Browser and Internet to the SMR Server 750, which updates the Doctor's mobile device in the Active Device Table 760. Alternatively, if the server 750 created the PIN, it may update Active Device Table with the pin by itself, without communications from the Doctor's Phone App 707.

(3) Patient SMR Phone App 712 sends the PIN, which the Doctor gives to the patient, to SMR Server 750, requesting that Doctor's information be displayed on the screen of the patient's smart phone.

(4) The doctor's information is extracted from the Active Device Table and sent to by the SMR Server to the patient's device, where it is displayed to the patient. The patient could then review this displayed information visually on the screen of the mobile device and verify that it is indeed the doctor who the patient authorized to access patient's PHR data.

(5) The patient selects the Doctor on the touch screen of his mobile device. The processor on the patient's mobile device 710 recognizes that an input selection has been made and the Patient App stores patient's symmetric private crypto key 770 ("patient's private key") in the doctor's record, for the duration of the authorized access to the patient's PHR. Once the authorization expires or authorized access to PHR is accomplished, the serer will erase the patient's symmetric private key 770 or make it NULL in the table. In one of the embodiments, the patient's private key 770 is transmitted back to the SMR Server 750, where it is processed by the processor and stored, for the duration of the authorized access, in the Active Device Table's 760 entry or record for the Doctor's Device, shown as 780 in FIG. 7. In at least one embodiment, the patient's private key 780 is not stored permanently in the Active Device Table, but only remains stored for the duration of the authorized session or access for the authenticated doctor's device to the specific patient's PHR.

In accordance with at least one embodiment of the present invention, the patient requests a list of active doctor devices in the Active Device Table 760 and enters the PIN 709 that the doctor gives him—the patient can see the doctor record on the screen of his iPhone (or another mobile device) and can verify that it is the doctor's mobile device record that he is viewing. The patient then selects that record and clicks "authorize". This would send a request to the SMR Server to update the doctor's record with a copy of a certificate that would authorize the doctor to have access to the patient medical data, while the patient's and doctor's devices are in the proximity of the Node. Alternatively, the patient or the SMR system can set a time window during which the doctor's mobile device or computer is authorized to access PHR data of the patient.

In one embodiment, this certificate could have a time expiration of less than an hour—long enough for the doctor to update the necessary information but then expires, at which time doctor's access to PHR data for the patient is no longer permitted. Thus, the access can be limited to the patient being in the proximity of the doctor's WiFi node and for a limited time, or both. In other embodiments, the certificate could be set to expire as soon as the patient leaves the doctor's office or HCP facilities.

Step 5: Doctor Uses Certificate to View and Update Records

The Doctor's device App sends a request to SMR Server 750 to use the certificate (patient's private key) 780 temporarily stored in the Active Device Table entry for the access to patient's PHR, which is authorized for the Doctor's mobile device (placed there by the patient, as described in Step 4). The Doctor's SMR App then utilizes this key, or certificate as authorization and uses patient's private encryption key to decrypt patient's PHR on the server 750, re-encrypt the PHR using doctor's Asymmetric PKI key and download the patient medical records (PHR) to the doctor's mobile device for viewing. Similarly, the patient's private encryption key is used at the server 750 to encrypt any updates that are sent to it by the doctor from his or her mobile device 710. The Doctor updates patient's PHR, encrypt the updated data using server's public key and send it back to the SMR Server 750. At the server, this updated record, received from the doctor's device 710, is decrypted using server's private key, and then re-encrypted using patient's private symmetric key, for storage with the patient's medical records and data in the PHV (not shown). This update may be done live or in real-time, during patient's visit to the HCP's facilities. This way the patient may grant authorization for the use of his private key during patient's presence at the HCP's office, and terminate the authorization shortly thereafter. This allows for the upload of the latest medical records, which could then be used by the next HCP who treats the patient, at the pharmacy or at any other HCP location. In addition, the server may request digital fingerprint (or other digital authentication, like facial recognition, retina scan, etc.) from a person operating the doctor's mobile device and compare it to the digital fingerprint (or other digital authentication, like facial recognition, retina scan, etc.) of the doctor, which is stored in the database for the authorized HCPs. This assures that the correct HCP is authorized to access and view/update the patient's PHR. In addition to this, an alternative embodiment of the present invention may also use digital token exchange for confirmation and authentication of authorized access to patient's PHR, as described in connection with FIGS. 12 and 13 below.

Figure 8:
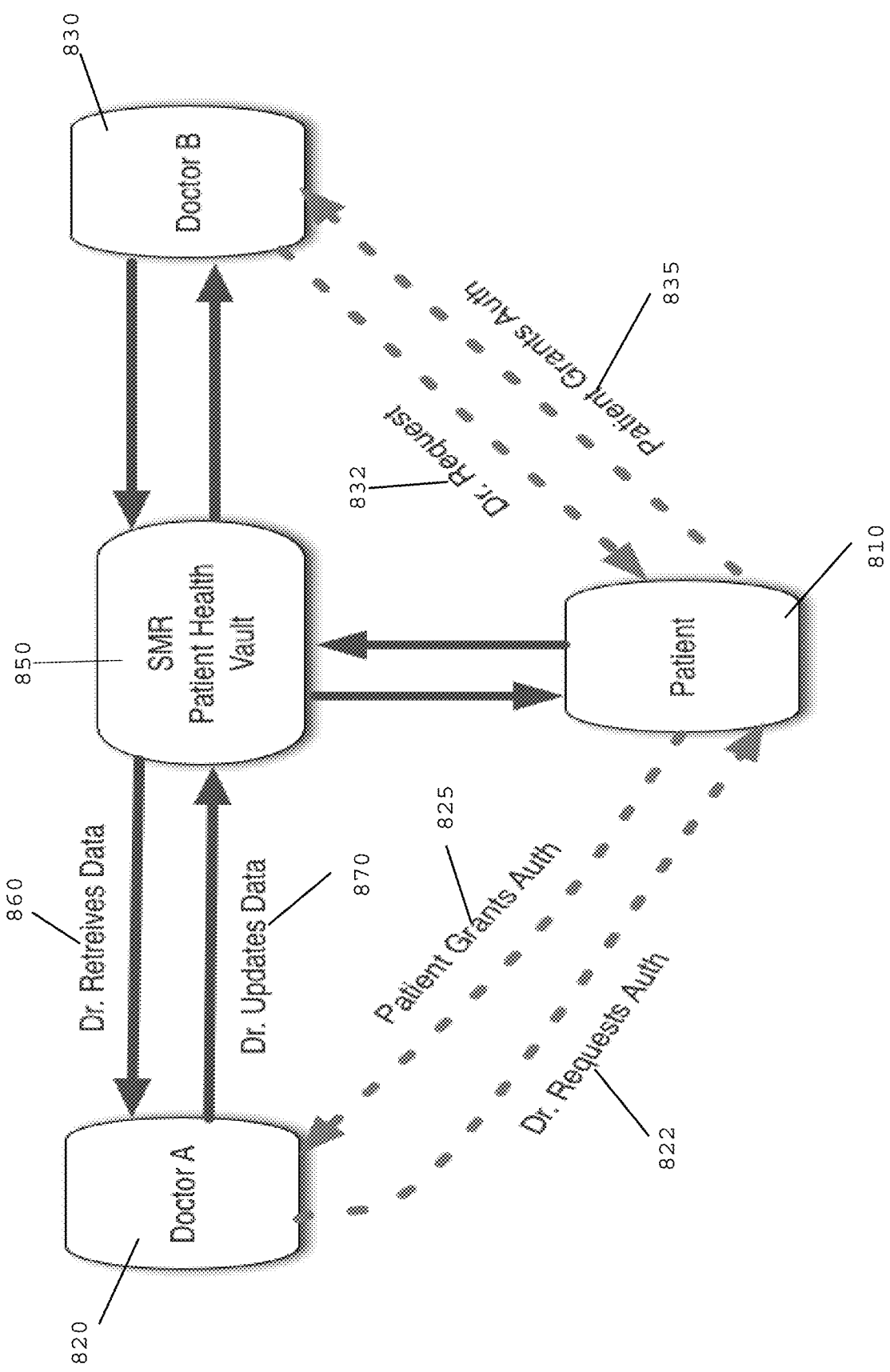
FIG. 8 illustrates a schematic diagram of the two-way data flow and authorization given by a patient to multiple HCPs to access and update the PHR data of the patient through the SMR server and SMR Patient Health Vault (PHV) data storage, in accordance with at least one embodiment of the present invention.

FIG. 8 illustrates the generalized process and system where the patient grants access to PHR to different HCPs or doctors in accordance with the present invention. In accordance with the embodiment shown in FIG. 8, the SMR PHV 850 becomes the central conduit of communications and access authorization to patient's PHR data for all doctors and HCPs. As shown in FIG. 8, the patient 810 utilizes the SMR software on its mobile device to provide Doctor A 820 and Doctor B 830, through the communication to the SMR software on their mobile devices or computers, located at each doctor's office (or multiple offices) with the permission or authorization to access Patient's PHR data stored in the SMR PHV 850. It should be noted that while FIG. 8 shows dotted lines to depict the authentication communications and authorization happening directly between each doctor 820 and 830 and the patient 810, in the actual system, all communications proceed through the SMR Patient HVS 850. When Doctor A requests authorization 822 to have access to the patient's PHR data, the patient may choose to grant 825 authorization by providing Doctor A with a "private key" or access to the Patient Key Vault, where the encryption key used by the patient 810 for access to his or her PHR is stored. In other circumstances, the patient 810 may require higher security, and respond to Doctor B's request 832 for access to PHR by providing a limited authorization 835 by providing patient's key or access to the keys in the Patient Key Vault for the patient 810 only when the patient is in the Doctor B's office, or for a specific set time limit following the visit. The presence of the patient in the Doctor's Office can be determined by the use of Proximity Detection components of the present system that are described above (not shown in FIG. 8). Additionally, digital fingerprint confirmation (or other digital authentication, like facial recognition, retina scan, etc.) may also be required to confirm that the person operating the doctor's mobile device is the actual doctor authorized to access PHR by the patient.

The update of the PHR data 870 and access to PHR data 860 are provided for each Doctor, who has obtained the "private key" from the patient 810, or who obtained an authorization, sent by the patient to the SMR server to allow a particular authorized and authenticated HCP to gain access to the encrypted PHR for that patient. This is accomplished in part through the processor and display screen on the doctor's computer, and also through the web browser software, which allow for the display of the patient's PHR on the Doctor's computer display screen (on the mobile device or on a desktop computer). In order to send, update or upload the patient's PHR data, the following actions take place:

(1) The HCP may utilize the SMR Doctor client mobile device or computer, equipped with the Web browser, to view and enter patient's data using a screen, virtual or actual keyboard, mouse or other computer data input device.

(2) Alternatively, the HCP may utilize its Electronic Health Record (EHR) computerized system to select the specific patient 810 PHR records in the EHR, use the native EHR function to export the data to a local disk or data storage device or RAM on the HCP's computer or mobile device, and then use an SMR utility to push or send one or more PHR records of that patient to the SMR PHV 850 in one operation or transfer.

(3) Alternatively, the SMR transfer and access may be fully integrated into the HCP's EHR system, so that the HCP simply selects certain PHR data records for the patient 810 within ECH system, and automatically pushes or sends them to the SMR PHV 850 for storage. This process may require some customization and integration of the EHR system at the HCP location with the SMR system of the present invention.

It should be noted that either the proximity detection or electronic token exchange or any other electronic tools may be used by the patient to provide the authorization to access that patient's PHR data stored in the PHV in accordance with the present invention. Also, the extraction process from the EHR to PHV may be automated, with programmed robot processes for extraction and movement of patient data from HER. It may also preform the move automatically in batch or one record or one patient at-a-time.

FIG. 9 illustrates another aspect of at least one embodiment of the present invention, where the SMR system according to the present invention not only keeps the anonymous encrypted PHR data for the patients, but also provides separate Key Bank (or Vault) Service 950 and storage of the patient's crypto key for access to patient's PHR in the Key Vault Database 955. It also demonstrates use of the Patient ID Mapping Service 960 for accessing Patient ID Directory or database 965, as an additional security layers of protection, to access patient's PHR in the PHV 975. As further illustrated in FIG. 9, the patient's mobile device may be equipped with iOS operating system 910 or Android operating system 920. and will also have a computer processor, internal and possibly external memory, virtual or real keyboard and a computer display or screen. It may run and execute by a processor the computer instructions of the computer app for accessing PHV on the patient's mobile device. The patient's mobile device may access the PHV Service 970, Key Bank Service 950 and Patient ID Mapping Service 960 through the Web Browser software 930 on the patient's mobile device, or alternatively directly, through the specialized app on the mobile device. If proceeding through the Web Browser, the patient's mobile device acquires the PHV Service 970 through the PHV Web Server 972. Similarly, it obtains the Key Bank Service 950 through the Key Bank Web Server 952, and Patient ID Mapping Service 960 through the Map Web Server 962. The Key Bank Service 950 provides a secure electronic Key Vault or key database 955 for patients that choose to keep a copy of their PHV private crypto key in the secure remote location or vault, instead of, or in addition to, keeping their keys in their own possession, on their computer or mobile device(s). A properly formatted request with correct verified credentials of the patent will be processed by the Key Bank Service 950, accessing Key Vault 955 and providing the key directly to the PHV Service 970, as shown by the arrow from the Key Bank Service 950 to PHV Service 970. The Patient ID Mapping Service 960, will authenticate a properly formatted request with the proper patient key and correct verified credentials of the patient, and access the Patient ID Directory 965, to obtain and provide the PHV account number (or some account identifier) for a given patient based at least partially on the private crypto key from the Key Bank Service 950 for a particular patient. This account id or data may be used together with the patient's key obtained in the Key Vault 955 in order to correctly identify the specific PHR for that patient in the PHV 975. In such system, even if someone who is not authorized intercepts the decrypted PHV data record when it is being transmitted by the PHV Service, this information would be practically useless without correlating it to the proper patient account, which would not be possible without going through the Patient ID Mapping Service 960. Thus, it would add yet another level of security for the PHV data access and update capability.

Figure 10:
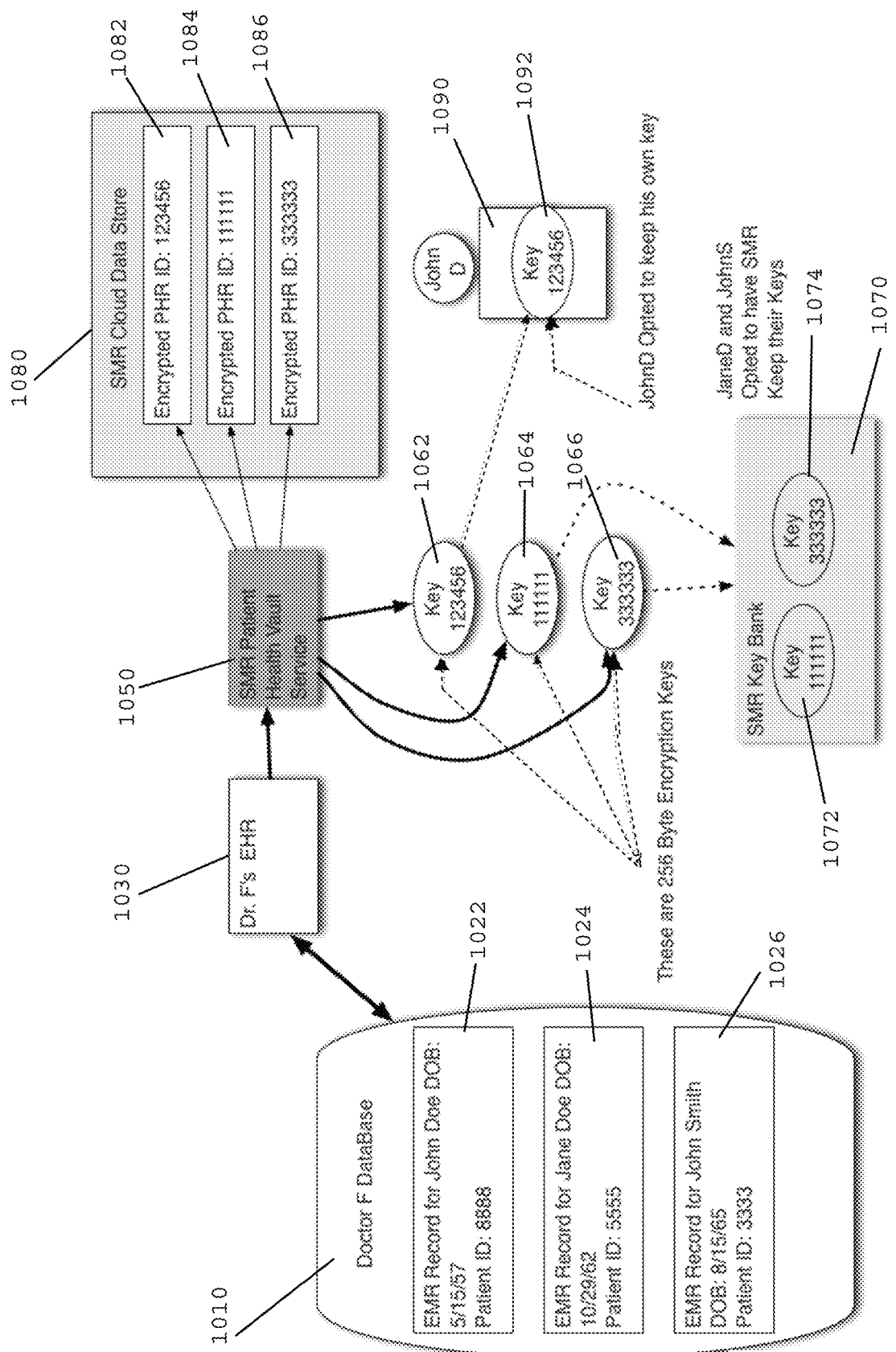
FIG. 10 illustrates a diagram and the process flow of patient's PHR data transfer from the HCP's proprietary EMR system to the PHV database in accordance with at least one embodiment of the present invention.

FIG. 10 illustrates the process of PHR data being extracted from the HCP's EHR system in bulk and the creation of PHV records for each of HCP's patients. The Doctor's (HCP's) EHR database 1010 contains medical records of several patients, shown as three different patents EMR medical records 1022, 1024 and 1026 respectively. The processor on the HCP's server where the database 1010 resides operates to upload the PHR records through the Doctor's (HCP's) interface 1030 to Patient PHV Service/server 1050, for storage in the PHV database 1080, which is preferably a cloud-based data storage or database. At the express instructions from each patient, the patient crypto keys for access to PHV data of that patient may be given directly to the patient, upon the upload of the PHV data in to vault, or can be place in the Key Bank 1072. As depicted in FIG. 10, keys for two patients 1064 and 1066 are stored in the Key Bank 1070, as key records 1072 and 1074, while the third crypto key 1062 is sent to the patient's mobile device or computer 1090 and stored in the internal or external memory 1092. The PHV records of each patient 1082, 1084 and 1086 are encrypted and stored in the PHV database or data store 1080. In accordance with at least one embodiment of the present invention, the PHV does not keep or store the patient's private key in the database or memory. After the PHR data for a patient is encrypted with the patient's key and stored in the PHV, PHV server erases the copy of the key. This way only the patient retains permanent control of the key for access to that patient's PHR in the PHV database.

Figure 11:
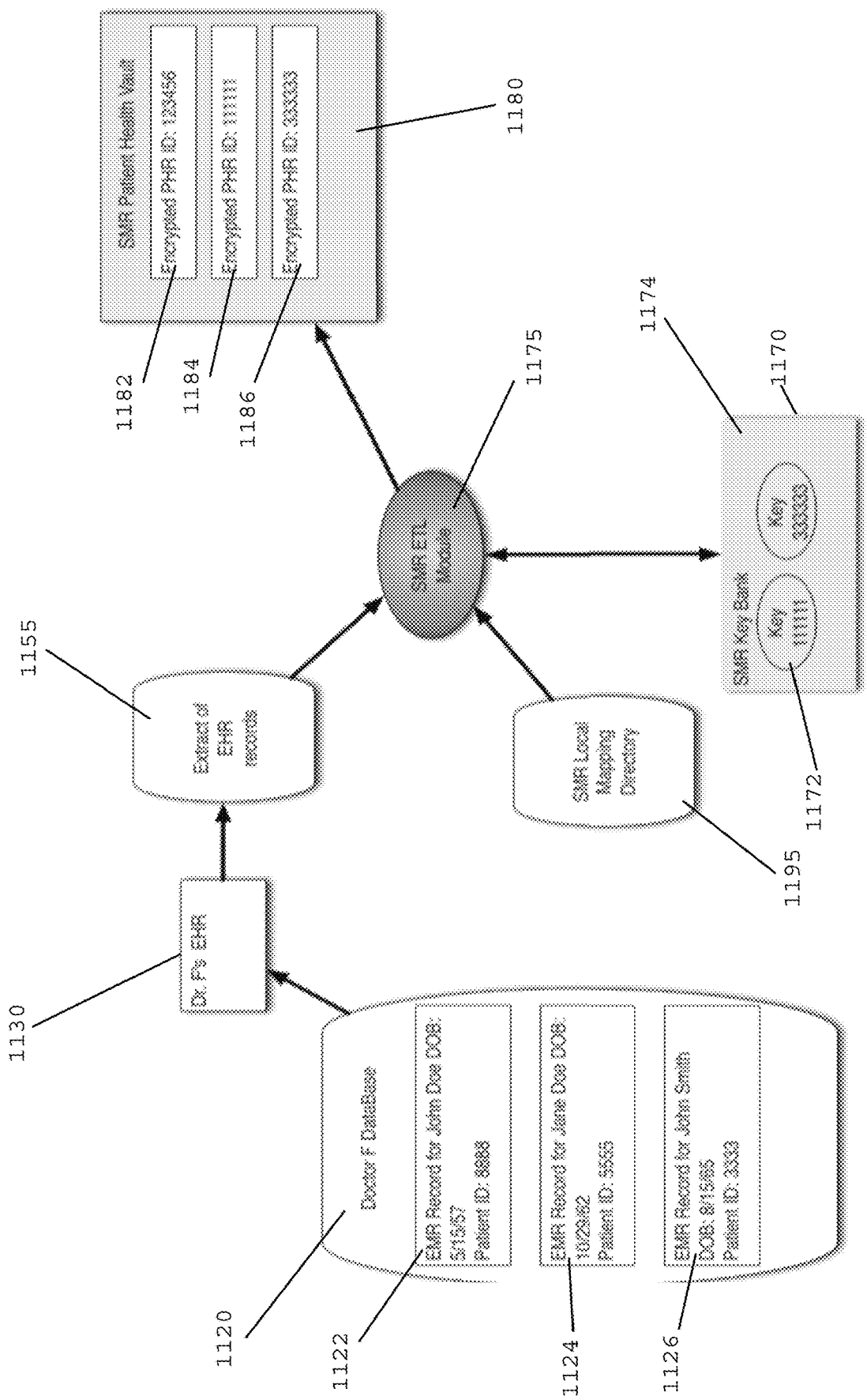
FIG. 11 illustrates a diagram and the process flow of the patient's PHR data transfer and mapping of records from the doctor's EMR system to the PHV Cloud-Based database in accordance with at least one embodiment of the present invention.

FIG. 11 illustrates the process of PHR data extraction of the patient EHR medical records 1122, 1124 and 1126 from the HCP's EMR database 1110, transmission of the patient medical records through the EHR interface 1130 for storage in the PHV database 1180 as encrypted PHR data records 1182, 1184 and 1186 for each patient. In addition to the process steps for the EHR to PHV transfer shown in FIG. 11, the embodiment shown includes the extraction of the HER data 1155 and transmission to the ETL (extract, transmit, load) module 1175, wherein the PHR data is filtered, removing all patient identifying information, and the individual PHR record of the patient is stored in the PHV 1180 database as "anonymous" PHR record, identified only by the account number or id. Thus, to be able to access and obtain the PHR records in the anonymous PHV for a particular patient, the requesting server must have the patient key, and the account id. The Local Mapping Directory 1195 provides the correct account id for the patient to the ETL module 1175, which allows to identify the PHV records for that particular patient by processing patient id data and providing the account number or id to the ETL Module 1175 for that patient. The provided account number or id, together with the patient's key from the Key Bank 1170 will allow ETL Module to locate, access and decrypt the PHR records for a particular patient stored in the anonymous PHV database 1180. Thus, the access to records in the anonymous PHV database 1180 is accomplished using the patient's private crypto key stored in the Key Bank 1170 and account or location id (or location key), which is obtained from the Local Mapping Directory 1195 using some patient-specific identification information, password or some credential and identity verification scheme. The doctor may choose to create his own secure PHV 1180 of all patient records in the Doctor's Database 1110 and EHR 1130. In order to accomplish this migration of the PHR data in Doctor's HER database to the PHV 11180, the doctor or HCP will create and use his own private crypto key for encrypting all patient records 1122, 1124 and 1126 in the Doctor's Database 1110, and storing them in the encrypted format in the PHV as 1182, 1184 and 1186. In addition, the SMR Local Mapping Directory 1195 will receive information about all patients in the Doctor's Database 1110, and will map the patient id to the new location id or location information for each patient record in PHV 1180. The doctor or HCP may also store doctor's private key for the PHV database of all his EHR patients in the SMR Key Vault 1170.

When the doctor or HCP is requested to share or provide his PHV-stored information to the particular patient, the records corresponding to that particular patient are extracted from the PHV and decrypted using doctor's private key and location id (or location key) provided by the SMR Local Mapping Directory 1195, identifying the records of that patient that doctor moved from the EHR to PHV 1180. Once decrypted using doctor's private key, the PHR patient's records may be sent to the patient, who then may update or load this PHR data into his own PHV in 1180, at a new location id (or location key) corresponding to the patient's own PHR data, which he or she can then share with different HCPs. In order to accomplish this, the PHR data of the patient, which was provided by the doctor, is re-encrypted with patient's own private key, and stored back at the new location id (or existing location id for the patient's own PHV data) in the PHV 1180. In addition, the location id (location key) of the patient's PHV records will be updated and stored in the SMR Local Mapping Directory 1195, thereby allowing location of the patient's own copy or version of his or her own PHR records, which can be shared with multiple doctors and HCPs. The patient may also choose to place his private crypto key used for the encryption and decryption of patients PHR records in the SMR Key Bank 1172. This allows each patient to remotely maintain access to one key that allows doctors and HCPs to access patient's PHR stored in PHV 1180. The patient does not need to maintain and remember numerous passwords or security ids for different HCP databases where some portions of that patient's PHR is kept. It also provides each patient with the control of access to this or her PHR, thereby solving the problem of having multiple HCPs maintain and update their records for that patient with the latest PHR information, such as treatments by other doctors, changes in prescriptions, new prescribed treatments and medications, on-going therapies and referrals to other physicians, etc. It also solves the problem for the patient in having to coordinate information stored for that patient in different HER and other databases or records maintained by each HCP who treats that patient.

Figure 14:
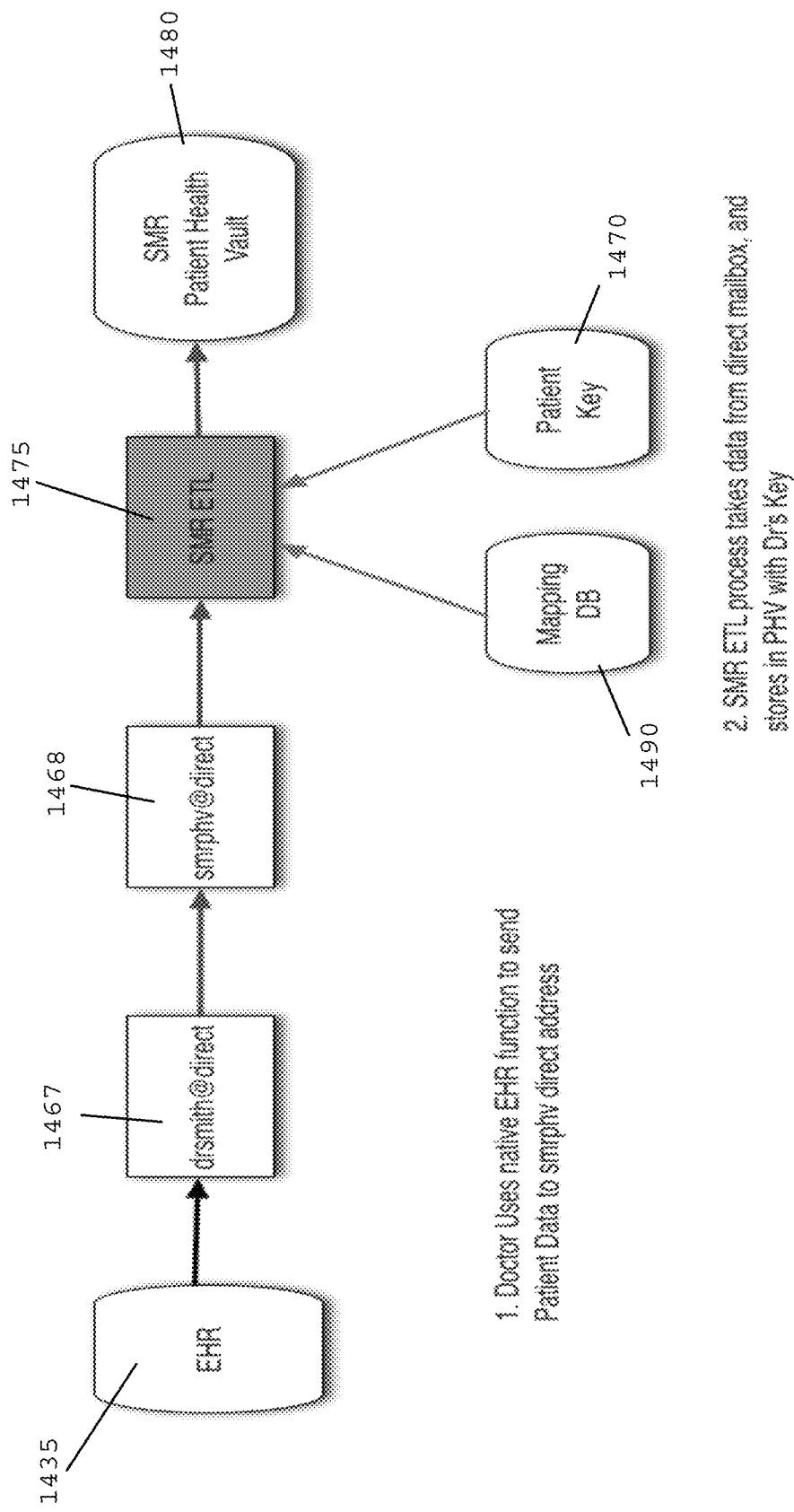
FIG. 14 illustrates a diagram and the process flow of the update process from the doctor's EHR to the secure Patient Health Vault in accordance with at least one embodiment of the present invention.

FIG. 14 further illustrates the process for pushing data from the HCP's EHR database 1435 to the PHV database 1480, where the doctor or HCP uses Direct Message transfer to send patient data from the EHR database 1480 to doctor's direct address 1467 and then to the PHV direct mailbox address 1468. Then the patient PHR is sent to the ETL module 1475, which receives the data from the PHV direct mailbox and stores it in the PHV database 1480 with the crypto key. The patient key 1470 is obtained from the patient or Key Vault (not shown), and the account id is obtained from the Mapping Database 1490 using patient identification and verification data. Thus, the PHR records stored in PHV are encrypted with patient's crypto key and account id identifier for the patient, to allow linking of the stored data with the patient. Alternatively, the PHV can be encrypted with the doctor's key, if doctors intends to migrate the patient database kept in the doctor's EHR to PHV, accessible by the doctor.

In another embodiment and feature of the present invention, the doctor or HCP can create and maintain its own PHV database for a patient, and push or transfer PHR data for that patient from the doctor's PHV database to the patient's PHV database. When storing data in the HCP's PHV, the doctor or HCP would encrypt it with doctor's own crypto key, and when it is transferred to copied to the patient PHV, the data is re-encrypted with the patient's crypto key. Alternatively, the PHV server may accept a request from the doctor to transfer the PHR data from the doctor's PHV to patient's PHV, and instead of actually performing some physical transfer, only decrypt the PHR using doctor's key, and re-encrypt it using patient's key, without any actual move to another database or copying of the PHR data.

In at least one embodiment, the present invention may also utilize the PHV for storing patient's data, where all private and personal information is removed. For example, the automated computerized system or the AI on the server may extract the patient's medical records from multiple HCPs' databases, remove all patient's private information or patient identification information. The de-privatized/de-personalized or anonymous medical data can then be stored in the PHV and shared with others for research and other purposes. Thus, the PHV can store and maintain not only the patient's medical records for use by treating providers, but also a de-privatized/de-personalized version of the medical data that can be shared with researchers and other public sources.

The present invention also allows the patient to establish a trustee (or a medical proxy or representative) for granting access to patient's medical records and for granting access rights to HCPs and time-based and limited access to the patient's PHV and medical records. The patient or patient's representative or appointed trustee can also grant access to the de-privatized/de-personalized patient data (with private identification information removed) in the similar manner.

FIG. 12 illustrates a general scheme and process for the authorization process, to authorize and allow access to patient PHR stored in PHV 1280. It illustrates authorization through the exchange of tokens (electronic or digital), or some specific digital codes or identifiers that allow the HCP and HCP mobile device 1220 to receive authorization to access patient data in PHV 1280. At Step 1, the patient or the application software on the patient mobile device 1210 informs the doctor or communicates to the doctor's mobile device 1220 with instructions to go to the SMR server, through the Internet, and request patient's access to that patient's PHR stored in the encrypted format in the SMR PHV 1280. As Step 2, the doctor or HCP operates his or her mobile device 1220 or computer device, equipped with computer screen, keyboard, input-output device like computer mouse, computer processor and memory to request access from the SMR Server 1250 through the Web browser software 1230. Alternatively, the access and connection to the SMR Server 1250 could be accomplished through an app software executing on the doctor's mobile device of computer 1220 or on the connected or distributed network. As Step 3, the doctor's mobile device sends through the Internet and Web Browser 1230 operating on it a request to the SMR Server 1250 to provide access (for reading and/or update) to the patient's PHR stored in the SMR PHV 1280. In order to do so, the doctor needs to obtain patient's authorization. As Step 4, the SMR Server 1250 sends back to the doctor's mobile device a digital token or id (shown as token 123456 on FIG. 12). Once the digital token is returned by the SMR Server 1250 to the doctor's mobile device 1220, it is then communicated from the doctor's mobile device (or computer) to the patient mobile device 1210, as Step 5. Then, as Step 6, the patient operates his mobile device or computer to access SMR app or SMR Server through the Internet and request access to patient's PHR data stored in PHV 1280 for the doctor or HCP identified by the received digital token 123456. The patient may complete this requested operation through the application software executing by a processor on the patient's mobile device. Alternatively, the patient may access the SMR Server 1250 through the Internet browser, and send the request as part of HTML or some other known Web-based communication protocol. As Step 7, the SMR Server 1250 receives patient's authorization for the doctor's access to patient's PHR in the PHV 1280, and also processes the "doctor token," digital token received from the doctor (shown as Token 123456). Once processed, the Server 1250 returns back to the patient mobile device 1210 a different digital token or id (shown as Token 222222 on FIG. 12.) This "patient token" is then sent from the patient's to doctor's mobile device, or communicated to the HCP who enters it through an input-output interface into the doctor's mobile device 1220, and then through the Web browser 1230 (or, alternatively, through the app executing on the doctor's mobile device) to the SMR Server 1250. Once the SMR Server 1250 receives both the "patient token" and "doctor token," where "doctor token" is sent to SMR Server 1250 by the patient's mobile device 1210, and "patient token" is sent to SMR Server by the doctor's mobile device 1220, the authentication process is complete, and SMR Server 1250 determines that the patient has properly authorized the doctor to access patient's PHV stored in SMR PHV 1280.

FIG. 13 illustrates a diagram and the process flow of the process to allow the doctor 1320 to access and view the specific patient's PHR data stored in the PHV database 1380 when the HCP was already granted access by the patient 1310 in accordance with at least one embodiment of the present invention, or in accordance with the authorization process described above in connection with FIG. 12.

The PHV 1380 requests patient's symmetric crypto key and account or record id from the SMR App 1315 executed by the computer processor on the patient's mobile device. The SMR App 1315 processes the symmetric crypto key entered by the patient 1310 or previously stored on the patient's mobile device. The patient's private crypto key, shown as Key="keyxxxx" in FIG. 13 is sent to the PHV together with the account or record id (888888) identifying the patient's account and records. Both are encrypted for secure transmission with the PHV server's public asymmetric public key that is sent to the patient's mobile device by the PHV 1380. The PHV 13808 can then decrypt the transmitted data (containing private crypto key of the patient and account or record id information) using its own private PHV asymmetric PKI server key. Then, the PHV 1380 can use the patient's key (keyxxx) to decrypt the encrypted PHR data 1386, located using the account or record id that allows to access patient's records in the PHV database. The patient's private symmetric crypto key is used to decrypt the encrypted PHR data 1386 for that patient. The web server of PHV 1330 can then re-encrypt the PHR data for the patient with the asymmetric public key of the HCP and send it to HCP's browser 1325 on the HCP's mobile device or desktop computer. Then, the HCP app processor can execute software to use HCP's asymmetric private key to decrypt the transmitted data and view it on the screen of the doctor's mobile device, or send for viewing to a monitor, or to as printer (for printing).

The tracking and management screens used by the SMR server in accordance with at least one embodiment of the present invention may proceed as follows. The SMR server may track and account for all users that are singed into and operate the SMR server, including all patients, doctors and administrators. It may show a particular display screen generated on the server to indicate the role of each person and display the functions that are permitted for each person.

For example, the patient is permitted to grant access to a doctor. The patient may see a menu function to grant access to a doctor. When granting access, the patient may provide a digital token to the doctor, and may then be asked to enter the code or digital token or code to provided by the doctor to the patient. If this token or code is accepted, the patient would receive a message that the 2-way access was enabled, and this information may be reflected for the patient on the server, and can be shown in the management screen. If the exchanged digital tokens or codes do not match, the server will prompt the patient to re-enter the doctor's code or digital token.

For the doctor, the server will provide a message or screen indicating that the patient's code was verified by the server, and that doctor should give the digital token or code provided by the server to the patient. Once the patient receives and enters this code, the doctor may receive a new message, indicating that the 2-way access was enabled.

Additionally, the server may provide a separate menu or Web page to the patient for revoking the access to patient's PHR for a particular HCP. It may send and display on the patient's mobile device the information about or listing of all HCPs that are currently authorized by the patient to access his or her PHR. Then, the patient may choose to revoke access for a particular HCP. This revocation input is sent back to the server, where the active device table entry for that HCP is revised and the private symmetric key of the patient is deleted, thereby no longer allowing HCP to decrypt and read/update the patient's PHR kept in the PHV.

For doctors, the server may display and allow menu selection to select either the access/read of the patient's PHR or the update. For both, the read and update, an authorization from the patient is required, and the doctor is informed about the status of this authorization request. Internally, the server must receive the patient's private crypto key for decryption of the patient's PHR in the PHV. It also needs location id (or location key) for locating the patient's records in the PHV. If all this is provided by the patient, then the server may inform the doctor by a message that access to patient's PHR is established, and allow selection of either reading or to update function.

The above embodiments and illustrative descriptions of the application of the principles of the present invention are intended to enable a person skilled in the art to make or use the disclosed invention. They are not intended to be either exclusive, exhaustive or limiting on the scope of the invention described and claimed herein. Other variations or modification could be used and applied by a person skilled in the art without deviating from the scope and spirit of the present invention. Such modifications and alternatives arrangements are not intended invention to be outside the scope of the present invention and are intended to be covered by it. The invention title and abstract are not intended to limit the claimed invention or cover multiple embodiment and all various features of the claimed invention.

It will be understood by those skilled in the art that each of the above steps or elements of the system will comprise computer-implemented aspects, performed by one or more computer components described herein. Any or all of the steps of the recited methods may be performed electronically. Any or all steps may be performed electronically— either by general or special purpose processors implemented in one or more computer systems such as those described herein.

It will be further understood by one of ordinary skill in the art that the specific embodiments and examples in the specification are presented for illustrative purposes only, and are not intended to limit the scope of the disclosure. Accordingly, it will be understood that various embodiments of the present system described herein are generally implemented as a special purpose or general-purpose computer including various computer hardware as discussed in greater detail below. Embodiments within the scope of the present invention also include computer-readable media for carrying or having computer-executable instructions or data structures stored thereon. Such computer-readable media can be any available media which can be accessed by a general purpose or special purpose computer, or downloadable through communication networks.

By way of example, the computer-readable media can comprise physical storage media such as RAM, ROM, flash memory, EEPROM, CD-ROM, DVD, or other optical disk storage, magnetic disk storage or other magnetic storage devices, any type of removable non-volatile memories such as secure digital (SD), flash memory, memory stick etc., or any other medium which can be used to carry or store computer program code in the form of computer-executable instructions or data structures and which can be accessed by a general purpose or special purpose computer, or a mobile device.

When information is transferred or provided over a network or another communications connection (either hardwired, wireless, or a combination of hardwired or wireless) to a computer, the computer properly views the connection as a computer-readable medium. Thus, any such a connection is properly termed and considered a computer-readable medium. Combinations of the above should also be included within the scope of computer-readable media. Computer-executable instructions comprise, for example, instructions and data which cause a general purpose computer, special purpose computer, or special purpose processing device such as a mobile device processor to perform one specific function or a group of functions.

The persons skilled in the art will understand the features and aspects of a suitable computing environment in which aspects of the invention may be implemented. Although not required, the inventions are described in the general context of computer-executable instructions, such as program modules or engines, as described earlier, being executed by computers in networked environments. Such program modules are often reflected and illustrated by flow charts, sequence diagrams, exemplary displays, and other techniques used by those skilled in the art to communicate how to make and use such computer program modules. Generally, program modules include routines, programs, objects, components, data structures, etc. that perform particular tasks or implement particular abstract data types, within the computer. Computer-executable instructions, associated data structures, and program modules represent examples of the program code for executing steps of the methods disclosed herein. The particular sequence of such executable instructions or associated data structures represent examples of corresponding acts for implementing the functions described in such steps.

Those skilled in the art will also appreciate that the invention may be practiced in network computing environments (including, without limitation, the LAN, WAN, distributed networks, cloud-based, etc.) with many types of computer system configurations, including personal computers, hand-held devices, multi-processor systems, microprocessor-based or programmable consumer electronics, networked PCs, minicomputers, mainframe computers, and the like. The invention is practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

In at least one example, an exemplary system includes a general purpose computing device in the form of a conventional computer, including a processing unit, a system memory, and a system bus that couples various system components including the system memory to the processing unit. The computer will typically include one or more magnetic hard disk drives (also called "data stores" or "data storage" or other names) for reading from and writing to. The drives and their associated computer-readable media provide nonvolatile storage of computer-executable instructions, data structures, program modules, and other data for the computer. Although the exemplary environment described herein employs a magnetic hard disk, a removable magnetic disk, removable optical disks, other types of computer readable media for storing data can be used, including magnetic cassettes, flash memory cards, digital video disks (DVDs), Bernoulli cartridges, RAMs, ROMs, and the like.

Computer program code that implements most of the functionality described herein typically comprises one or more program modules may be stored on the hard disk or other storage medium. This program code, as is known to those skilled in the art, usually includes an operating system, one or more application programs, other program modules, and program data. A user may enter commands and information into the computer through keyboard, pointing device, a script containing computer program code written in a scripting language or other input devices (not shown), such as a microphone, etc. These and other input devices are often connected to the processing unit through known electrical, optical, or wireless connections.

The main computer that effects many aspects of the inventions will typically operate in a networked environment using logical connections to one or more remote computers or data sources, which are described further below. Remote computers may be another personal computer, a server, a router, a network PC, a peer device or other common network node, and typically include many or all of the elements described above relative to the main computer system in which the inventions are embodied. The logical connections between computers include a local area network (LAN), a wide area network (WAN), wireless LANs (WLAN), distributed networks, cloud-based networks, etc. that are presented here by way of example and non-limitation. Such networking environments are commonplace in office-wide or enterprise-wide computer networks, intranets and the Internet.

When used in a LAN or WLAN networking environment, the main computer system implementing aspects of the invention is connected to the local network through a network interface or adapter. When used in a WAN or WLAN networking environment, the computer may include a modem, a wireless link, or other means for establishing communications over the wide area network, such as the Internet. In a networked environment, program modules depicted relative to the computer, or portions thereof, may be stored in a remote memory storage device. It will be appreciated that the network connections described or shown are exemplary and other means of establishing communications over wide area networks or the Internet may be used.

Calculations and evaluations described herein, and equivalents, are or may be performed electronically. Other components and combinations of components may also be used to support processing data or other calculations described herein as will be evident to one of skill in the art. A computer server may facilitate communication of data from a storage device to and from processor(s), and communications to computers. The processor may optionally include or communicate with local or networked computer storage which may be used to store temporary or other information. The applicable software can be installed locally on a computer, processor and/or centrally supported (processed on the server) for facilitating calculations and applications.

In view of the foregoing detailed description of preferred embodiments of the present invention, it readily will be understood by those persons skilled in the art that the present invention is susceptible to broad utility and application. While various aspects have been described in the context of a preferred embodiment, additional aspects, features, and methodologies of the present invention will be readily discernible from the description herein, by those of ordinary skill in the art. Many embodiments and adaptations of the present invention other than those herein described, as well as many variations, modifications, and equivalent arrangements and methodologies, will be apparent from or reasonably suggested by the present invention and the foregoing description thereof, without departing from the substance or scope of the present invention. Furthermore, any sequence(s) and/or temporal order of steps of various processes described and claimed herein are those considered to be the best mode contemplated for carrying out the present invention.

Although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in a variety of different sequences and orders, while still falling within the scope of the present inventions. In addition, some steps may be carried out simultaneously.

The embodiments were chosen and described in order to explain the principles of the inventions and their practical application so as to enable others skilled in the art to utilize the inventions and various embodiments and with various modifications as are suited to the particular use contemplated. Alternative embodiments will become apparent to those skilled in the art to which the present inventions pertain without departing from their spirit and scope. The exemplary aspects and embodiments set forth herein are intended to be illustrative, not limiting. Various modifications may be made without departing from the spirit and scope of the disclosure.

What is claimed is:

1. A method of secure access to patient's medical data comprising the steps of:
 (a) authenticating the patient's mobile device on a remote server;
 (b) authenticating the health care provider's mobile device on the server;
 (c) automatically determining by electronic device proximity detection that the patient's mobile device is in a geographic proximity to a node located at the health care provider's location;
 (d) transmitting a request to a patient mobile device to authorize the health care provider's access to the patient's health care records stored remotely with respect to the location of at least one node at the health care provider's location;
 (e) obtaining said authorization from the patient for the health care provider to have access to the patient's health care records, wherein the authorization is at least partially based on the determined proximity of the patient's mobile device to the node at the health care provider's location;

(f) transmitting through a computer network to a processor on a remote server a patient's private electronic crypto key used for decryption of the patient's health care records stored remotely, wherein access to said crypto key is provided by the patient for a specified duration;

(g) receiving the patient's private crypto key by the processor on the remote server, wherein the key is utilized to decrypt the patient's health care records;

(h) obtaining an id of the patient's health care records by the processor on the remote server;

(i) utilizing the patient's private crypto key and the id of the patient's health care records to locate and decrypt the patient's health care record;

(j) utilizing asynchronous PKI encryption keys of the health care provider and the remote server to re-encrypt and securely transmit the patient's health care records to the health care provider for viewing and updating;

(k) storing the patient's health care records remotely with respect to the health care provider's location, encrypted with the patient's private crypto key;

(l) receiving from the health care provider an updated patient's health care record encrypted for safe transmission with the server's asynchronous PKI key;

(m) decrypting the updated patient health care records using servers' private PKI key;

(n) re-encrypting the updated patient health care records on the server with the patient's private crypto key; and (o) storing the updated encrypted records remotely.

2. The method of claim 1, further comprising the steps of:

(p) receiving a digital identification of a person operating the health care provider's mobile device and verifying that it matches stored digital identification of a health care provider that is authorized by the patient to access that patient's private health care records stored remotely; and (q) receiving a digital identification of a person operating the patient's mobile device and verifying that it matches stored digital identification of the patient or a person authorized by the patient to grant access to that patient's private health care records stored remotely.

3. The method of claim 1, further comprising the step of:

(r) maintaining a table of all node devices that are present in a health care provider facilities, wherein each node device operates a proximity detector for determining the geographic proximity of the patient's or the health care provider's mobile device to the node.

4. The method of claim 3, wherein the table of node devices stores the signal strength value of the wireless signal received by the node device from the patient's mobile device, and utilizing said signal strength value for determining the geographic proximity of the patient's mobile device to the node.

5. The method of claim 3, wherein the node operates in the indoor location at the health care provider's facilities and determines by processing the wireless signals from the patient's and health care provider mobile devices the presence of those mobile devices at that specific indoor location.

6. The method of claim 3, wherein the node receives wireless signals from the patient's and health care provider's mobile devices and uses position triangulation or time delay of the wireless signal process for determining actual proximity location of those mobile device with respect to the node in the health care provider's office.

7. The method of claim 1, further comprising the steps of:

(n) maintaining a separate Key Bank database for storing private crypto key of the patient;

(o) receiving and processing patient's identification information for access to the Key Bank database; and (p) upon authenticating the identity of the patient and patient's mobile device requesting access to the Key Bank database, transmitting the patient's private crypto key to the server for access by a patient-authorized health care provider to the encrypted patient health care records that are remotely stored in the remote electronic data storage and retrieval system.

8. A method of secure access to patient's medical data comprising the steps of:

(a) authenticating the patient's mobile device on a remote server;

(b) authenticating the health care provider's mobile device on the server;

(c) automatically determining by electronic device proximity detection that the patient's mobile device is in a geographic proximity to a node located at the health care provider's location;

(d) transmitting a request to a patient mobile device to authorize the health care provider's access to the patient's health care records stored remotely with respect to the location of at least one node at the health care provider's location;

(e) obtaining said authorization from the patient for the health care provider to have access to the patient's health care records, wherein the authorization is at least partially based on the determined proximity of the patient's mobile device to the node at the health care provider's location;

(f) transmitting through a computer network to a processor on a remote server a patient's private electronic crypto key used for decryption of the patient's health care records stored remotely, wherein access to said crypto key is provided by the patient for a specified duration;

(g) receiving the patient's private crypto key by the processor on the remote server, wherein the key is utilized to decrypt the patient's health care records;

(h) obtaining an id of the patient's health care records by the processor on the remote server;

(i) utilizing the patient's private crypto key and the id of the patient's health care records to locate and decrypt the patient's health care record;

(j) utilizing asynchronous PKI encryption keys of the health care provider and the remote server to re-encrypt and securely transmit the patient's health care records to the health care provider for viewing and updating;

(k) storing the patient's health care records remotely with respect to the health care provider's location, encrypted with the patient's private crypto key;

(l) receiving at the server a location id of the patient's health care records stored remotely in an electronic data storage and retrieval system; and (m) utilizing the location id to find the remotely stored health care records of the patient, for viewing and update by a health care provider; wherein the remote electronic data storage and retrieval system that stores health records of the patient does not maintain or store any patient identifying information other than location id in a non-encrypted format.

9. The method of claim 8, further comprising the steps of:

(n) maintaining a separate database of location ids mapped to each registered patient;

(o) receiving and processing patient's identification information for access to the remote electronic data storage and retrieval system that stores health records of the patient; and (p) upon authenticating the identity of the patient and patient's mobile device requesting remote access to the remote electronic data storage and retrieval system, transmitting the location id for the patient's health care records that are remotely stored to the server, for read and update access to said records.

10. A computerized system for secure access to patient's medical data comprising:

a patient's computer device, having a processor, a keyboard, a display screen, a computer memory, storing and executing software code for authorizing access by health care providers to the patient's health care records remotely stored;

a health care provider computer device, having a processor, a keyboard, a display screen, a computer memory, storing and executing software code for requesting authorized access by that health care provider to the patient's health care records stored remotely with respect to the health care provider's location and for receiving the patient's health care records for viewing and updates;

a remote electronic data storage and retrieval system, storing patient's health care records encrypted with the patient's private encryption key, wherein the decryption of and access to said patient records may be performed only using that patient's private encryption key;

a remote access server, having a processor, a keyboard, a display screen, a computer memory, wherein the processor on the remote access server is disposed in communication with said server computer memory to issue and execute the computer instructions to:

authenticate the patient's mobile device on a remote server;

authenticate the health care provider's mobile device on the server;

automatically determine by utilizing the electronic device proximity detection that the patient's mobile device is in a geographic proximity to a node located at the health care provider's location;

transmit a request to a patient mobile device to authorize the health care provider's access to the patient's health care records stored remotely;

obtain and process said authorization from the patient for the health care provider to have access to the patient's health care records;

obtain a patient's private electronic crypto key used for decryption of the patient's health care records stored remotely, wherein access to said crypto key is provided by the patient for a specified limited duration;

obtain an id of the patient's health care records;

utilize said patient's private crypto key by a processor on the remote server to locate and decrypt the patient's health care records by the processor on the server;

utilize asynchronous PKI encryption keys of the health care provider and the remote server to re-encrypt and securely transmit the patient's health care records to the health care provider for viewing and updating;

store the patient's health care records remotely with respect to the health care provider's location, encrypted with the patient's private crypto key;

receive from the health care provider an updated patient's health care record encrypted for safe transmission with the server's asynchronous PKI key;

decrypt the updated patient health care records using servers' private PKI key;

re-encrypt the updated patient health care records on the server with the patient's private crypto key; and store the updated encrypted records remotely.

11. The system of claim 10, wherein the processor on the remote access server issues and executes additional computer instructions to:

receive a digital identification of a person operating the health care provider's mobile device and verifying that it matches stored digital identification of a health care provider that is authorized by the patient to access that patient's private health care records stored remotely; and receive a digital identification of a person operating the patient's mobile device and verifying that it matches stored digital identification of the patient or a person authorized by the patient to grant access to that patient's private health care records stored remotely.

12. The system of claim 10, further comprising:

a table of all node devices that are present in a health care provider facilities;

at least one node operating a proximity detector for determining the geographic proximity of the patient's or the health care provider's mobile device to that node.

13. The system of claim 12, wherein the table of node devices stores the signal strength value of the wireless signal received by the node device from the patient's mobile device, and wherein the signal strength value is utilized for determining the geographic proximity of the patient's mobile device to the node.

14. The system of claim 12, wherein the at least one node operates in the indoor location at the health care provider's facilities and determines by processing the wireless signals from the patient's and health care provider mobile devices the presence of those mobile devices at that specific indoor location.

15. The system of claim 12, wherein the at least one node receives wireless signals from the patient's and health care provider's mobile devices, and the system uses position triangulation or time delay of the wireless signal process for determining actual proximity location of those mobile device with respect to that node in the health care provider's office.

16. The system of claim 10, wherein the processor on the remote access server issues and executes additional computer instructions to:

receive at the server a location id of the patient's health care records remotely stored in the remote electronic data storage and retrieval system; and utilize the location id to find the health care records of the patient in the remote electronic data storage and retrieval system, for viewing and update by a health care provider; wherein the remote electronic data storage and retrieval system does not maintain or store any patient identifying information other than location id in a non-encrypted format.

17. The system of claim 16, further comprising:

a separate remote Mapping database of location ids mapped to each registered patient;

a local Mapping server for mapping location ids for each patient to that patient's health care records stored in encrypted format in the remote electronic data storage and retrieval system that stores health records of the patient;

wherein a processor on said local mapping server operates with computer memory to execute computer instructions to:

receive and process patient's identification information for access to the remote electronic data storage and retrieval system; and upon authenticating the identity of the patient and patient's mobile device requesting remote access to the remote electronic data storage and retrieval system, transmit the location id for the patient's health care records that are remotely stored to the server, for read and update access to said records.

18. The system of claim 10, further comprising:

a separate remote Key Bank database for storing private crypto key of the patient;

a remote Key Bank server for processing access to the Key Bank database;

wherein a processor on said Key Bank server operates with computer memory to execute computer instructions to:

receive and process patient's identification information for access to the Key Bank database; and upon authenticating the identity of the patient and patient's mobile device, transmitting the patient's private crypto key to the server for access by a patient-authorized health care provider to the encrypted patient health care records that are remotely stored in the remote electronic data storage and retrieval system.

* * * * *